(12) United States Patent
Koh et al.

(10) Patent No.: US 11,574,421 B2
(45) Date of Patent: Feb. 7, 2023

(54) METHODS AND SYSTEMS FOR PREDICTING PRESSURE MAPS OF 3D OBJECTS FROM 2D PHOTOS USING DEEP LEARNING

(71) Applicant: Visualize K.K., Tokyo (JP)

(72) Inventors: Chong Jin Koh, Las Vegas, NV (US); Kyohei Kamiyama, Tokyo (JP)

(73) Assignee: Visualize K.K., Tokyo (JP)

( * ) Notice: Subject to any disclaimer, the term of this patent is extended or adjusted under 35 U.S.C. 154(b) by 0 days.

(21) Appl. No.: 17/637,245

(22) PCT Filed: Aug. 27, 2020

(86) PCT No.: PCT/US2020/070465
§ 371 (c)(1),
(2) Date: Feb. 22, 2022

(87) PCT Pub. No.: WO2021/042124
PCT Pub. Date: Mar. 4, 2021

(65) Prior Publication Data
US 2022/0270297 A1 Aug. 25, 2022

Related U.S. Application Data

(60) Provisional application No. 62/892,909, filed on Aug. 28, 2019.

(51) Int. Cl.
*G06V 10/00* (2022.01)
*G06T 7/00* (2017.01)
(Continued)

(52) U.S. Cl.
CPC ............. *G06T 7/97* (2017.01); *A61B 5/1038* (2013.01); *G06N 3/08* (2013.01); *G06T 17/205* (2013.01);
(Continued)

(58) Field of Classification Search
CPC ............. G06T 7/50; G06T 7/55; G06T 7/529; G06T 7/543; G06T 7/564; G06T 9/002;
(Continued)

(56) References Cited

U.S. PATENT DOCUMENTS

| 6,129,681 A | 10/2000 | Kuroda et al. | |
| 2008/0115052 A1* | 5/2008 | Stevenson | G06F 3/0484 715/243 |

(Continued)

FOREIGN PATENT DOCUMENTS

| CN | 109567313 A | 4/2019 |
| CN | 109583273 A | 4/2019 |

OTHER PUBLICATIONS

Clever et al., "Bodies at Rest: 3D Human Pose and Shape Estimation from a Pressure Image using Synthetic Data" Computer Vision and Pattern Recognition, Apr. 2, 2020, pp. 1-18.
(Continued)

*Primary Examiner* — Amir Alavi
(74) *Attorney, Agent, or Firm* — American Patent Agency PC; Daniar Hussain; Xiaomeng Shi

(57) ABSTRACT

A structured 3D model of a real-world object is generated from a series of 2D photographs of the object, using photogrammetry, a keypoint detection deep learning network (DLN), and retopology. In addition, object parameters of the object are received. A pressure map of the object is then generated by a pressure estimation DLN based on the structured 3D model and the object parameters. The pressure estimation DLN was trained on structured 3D models, object parameters, and pressure maps of a plurality of objects belonging to a given object category. The pressure map of the real-world object can be used in downstream processes, such as custom manufacturing.

20 Claims, 16 Drawing Sheets

(51) Int. Cl.
*A61B 5/103* (2006.01)
*G06N 3/08* (2006.01)
*G06T 17/20* (2006.01)

(52) U.S. Cl.
CPC ............... *G06T 2200/08* (2013.01); *G06T 2207/20081* (2013.01); *G06T 2207/20084* (2013.01); *G06T 2207/30196* (2013.01)

(58) Field of Classification Search
CPC ........ G06T 3/4046; G06N 20/00; G06N 3/02; G06N 3/04; G06N 3/049; G06N 3/08; G06N 7/046
See application file for complete search history.

(56) References Cited

U.S. PATENT DOCUMENTS

| | | | | |
|---|---|---|---|---|
| 2009/0222996 | A1* | 9/2009 | Balonick | A47C 31/08 5/730 |
| 2010/0127983 | A1* | 5/2010 | Irani | G06F 3/03543 345/163 |
| 2011/0143811 | A1 | 6/2011 | Rodriguez | |
| 2014/0276235 | A1* | 9/2014 | Raniere | A61B 5/486 600/592 |
| 2015/0168238 | A1* | 6/2015 | Raut | G01N 27/223 702/42 |
| 2015/0304797 | A1 | 10/2015 | Rhoads et al. | |
| 2017/0046616 | A1 | 2/2017 | Socher et al. | |
| 2017/0367590 | A1 | 12/2017 | Sebe et al. | |
| 2018/0303399 | A1* | 10/2018 | Kahl | A61B 5/225 |
| 2018/0373959 | A1 | 12/2018 | Rhoads et al. | |
| 2020/0141819 | A1* | 5/2020 | Mamigonians | G01L 1/146 |
| 2020/0383641 | A1* | 12/2020 | Hwang | A61B 5/7278 |

OTHER PUBLICATIONS

Funk et al., "Learning Dynamics from Kinematics: Estimating 2D Foot Pressure Maps from Video Frames", Computer Vision and Pattern Recognition, Nov. 30, 2018, pp. 1-21.

Imaginea Labs, "Measuring feet using deep learning", Jul. 31, 2018, pp. 1-12. Available at: https://labs.imaginea.com/measuring-feet-using-deep-learning/.

Lauren Thomas, "Nike thinks you're probably wearing the wrong size shoe. Here's what it's doing to fix that", May 9, 2019, pp. 1-6. Available at: https://www.cnbc.com/2019/05/08/nike-is-launching-nike-fit-to-scan-your-feet-tell-you-your-shoe-size.html.

Nagendra et al., "Foot Pressure from Video: A Deep Learning Approach to Predict Dynamics from Kinematics", Nov. 30, 2018, pp. 1-14.

VFit, "The App that Fits Virtual Fit Shoe shopping", pp. 1-3. Available at: www.vfitshoes.com.

* cited by examiner

3D MODEL GENERATION
500
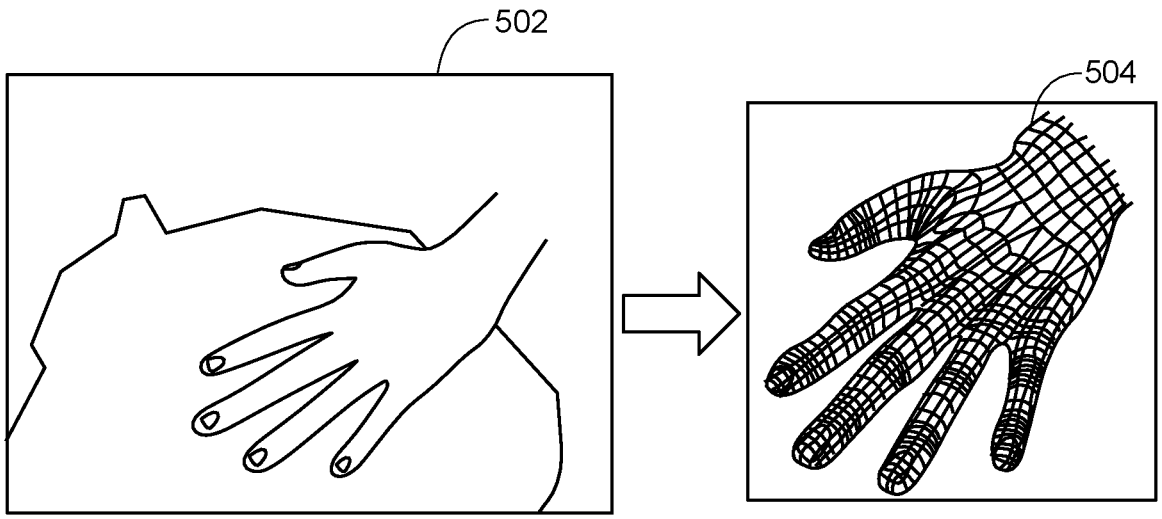
510
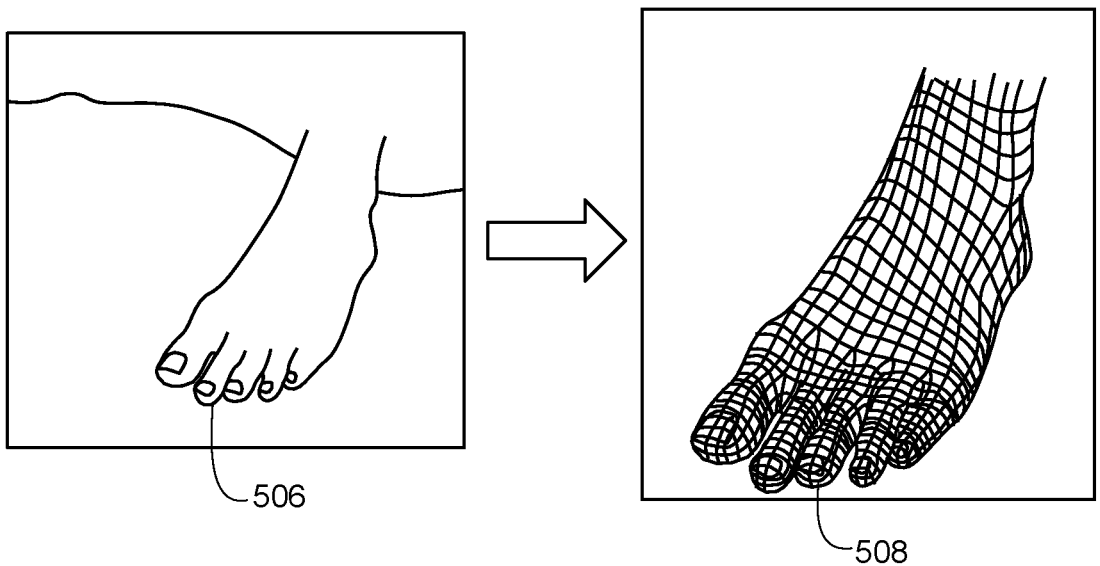
FIG. 5

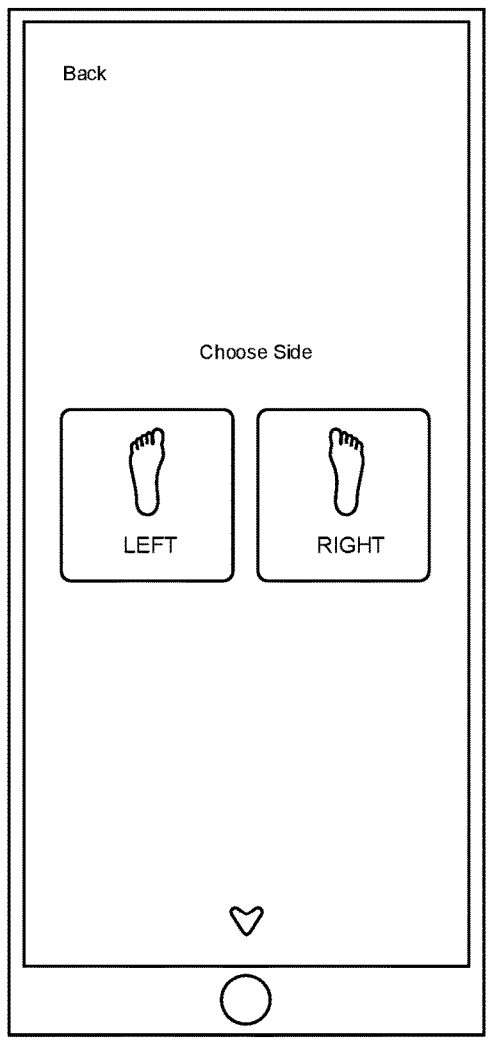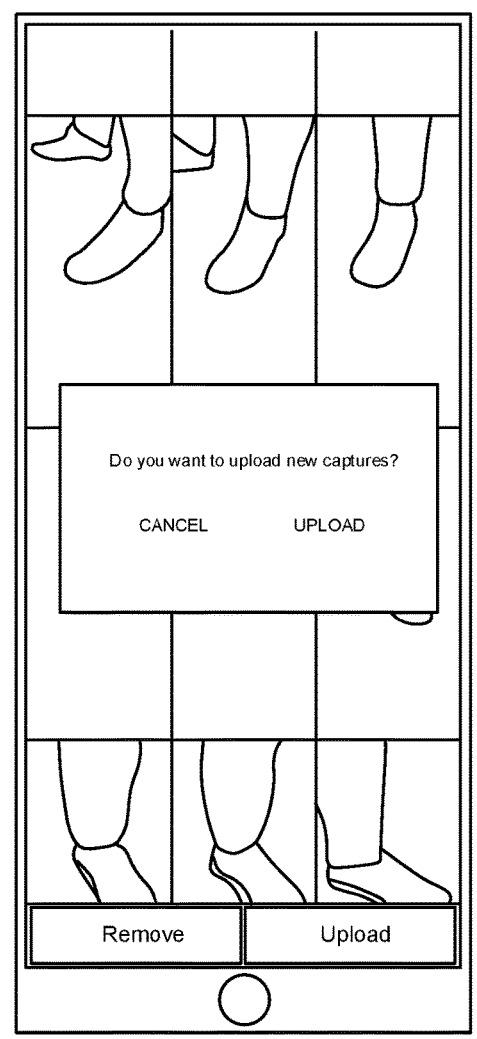
FIG. 13A                    FIG. 13B

METHODS AND SYSTEMS FOR PREDICTING PRESSURE MAPS OF 3D OBJECTS FROM 2D PHOTOS USING DEEP LEARNING

FIELD OF THE INVENTION

Embodiments are disclosed in the field of deriving pressure measurements for objects using deep learning, based on two-dimensional (2D) photographs of the objects, and optionally manufacturing of customized products from the object pressure measurements.

BACKGROUND OF THE INVENTION

The statements in the background of the invention are provided to assist with understanding the invention and its applications and uses, and may not constitute prior art.

Distribution of interface pressure—even between comparatively flat surfaces—is typically uneven with localized areas of peak pressure. For example, the pressure distribution in a human foot wearing a typical shoe is uneven with areas of localized pressure, which may be discomforting to the user. As a result, mapping and identifying the peak pressure points between two surfaces in a visual representation such as a pressure map offers insights to enhance product design and manufacturing quality in a wide variety of fields ranging from shoes, medical devices, prosthetics, to machines and automobile parts, and so on. Pressure maps can provide useful metrics such as the total force, peak pressures, center of force, etc., while serving as clear, visual representations of pressure distribution data in real-time or offline from recorded data. Modern pressure mapping systems are primarily constructed from thin, flexible sensors, scanning electronics that can scan thousands of sensing points, and associated software that generates maps of pressure distribution and other surface interaction data between two objects.

Pressure mapping finds uses in assessing component press fits and seals, machine design, and set up precision in industrial set ups. In the field of medical devices and prosthetics (e.g., braces), pressure maps can help assess comfort and a personalized and ergonomic fit. In addition, pressure mapping technologies can have numerous applications in myriad fields including high-speed impact testing, testing surface contact for thermal conductivity, semiconductor testing, testing the press fit and seal applications for ensuring that products and processes have proper fit and seal, and so on. In all these applications, generation of the pressure maps requires physical contact between the surfaces being tested, which in turn requires that the objects associated with the surfaces be brought into physical proximity to each other. In certain applications such as medical devices or prosthetics, where the users requiring customized products are not able to travel easily, bringing surfaces into physical proximity can be a problem.

It is against this background that the present invention was developed.

BRIEF SUMMARY OF THE INVENTION

This summary of the invention provides a broad overview of the invention, its application, and uses, and is not intended to limit the scope of the present invention, which will be apparent from the detailed description when read in conjunction with the drawings.

Methods and systems for predicting pressure maps of objects from 2D images of the objects are disclosed. A series of 2D images of a real-world object are initially obtained from a digital camera, a smartphone, a tablet device, or other computing device capable of capturing digital images. The series of 2D images can capture the object from different angles so that the form of the object is comprehensively recorded in the series of 2D images to the extent permissible by the two-dimensional nature of the images. In addition, object parameters of the object are received along with the 2D images. The object parameters that are collected can depend on the nature of the object. Generally, the object parameters can include certain object attributes such as size (including length, width, height, etc.), or other physical attributes such as weight, the material that the object is made of, etc. In an embodiment, the object can pertain to a human body part such as a person's hand or foot. When the object being recorded in the 2D images is a person's body part, parameters which are collected can include user parameters, such as the person's height, weight, body mass index (BMI), gender, racial profile, and so on.

The images and object parameters are processed by a three-dimensional (3D) model generation module that uses photogrammetry. Photogrammetry is a technique to extract reliable information about physical objects through photographic images. The series of 2D photographs which are collected are processed through a photogrammetry process to obtain a structured 3D model of the real-world object. In some embodiments, the photogrammetry process is followed by a keypoint Deep Learning Network (DLN) that generates 2D or 3D keypoints necessary for a subsequent topology transfer step (i.e., retopology or morphing). The retopology step uses the keypoints to morph a base mesh of the object into the structured 3D model. The structured 3D model of the real-world object may now be used to obtain measurements of the physical attributes of the object such as length, width, height, and so on. The structured 3D model, along with the object parameters, is provided to an object pressure estimation DLN trained to generate pressure maps of the object. Different object pressure estimation DLNs can be trained for different objects.

For example, a foot pressure estimation DLN can be trained to generate pressure maps of human feet with respect to the shoe on the ground or other reference surface. The pressure maps thus obtained can be used for various purposes, including but not limited to, studying the nature of the objects or enabling manufacturing of customized products. Referring again to the example of the person's foot, and according to one embodiment, the foot pressure map thus obtained can be used to manufacture customized foot accessories such as customized footwear or customized insoles, and so on. The person's attributes, the feet measurements, the 3D model of the foot, as well as the pressure map predicted by the foot pressure DLN, can be provided to a manufacturing system, such as a 3D printer, to obtain products customized to the person's foot. The pressure map prediction system disclosed and described herein therefore eliminates the need for expensive 3D foot scanners that are currently employed to obtain pressure maps of a person's feet. Moreover, patients with foot problems who may find it difficult to travel are saved the trouble of travelling to the locations of the 3D foot scanners for obtaining customized foot accessories, which can be shipped directly to the patient's home. In fact, the pressure map prediction system eliminates the need for pressure sensing hardware to obtain pressure maps of objects.

In order to be used in the pressure map prediction system, the object pressure estimation DLN has to be initially trained to generate the pressure maps from the various inputs including the 3D models of various objects, the object parameters of the objects, and the actual pressure maps of the objects. Different object pressure estimation DLNs can be trained with similar inputs for different objects. Of course, different object parameters can be collected for different objects. While the training examples are discussed with respect to the specific example of a human foot, it can be appreciated that similar training methodology can be applied to train the various object pressure estimation DLNs to generate pressure maps of various objects. In one embodiment, a training data set for the foot pressure estimation DLN is collected. The training data set can include the structured 3D models of different feet of different people generated from sets of 2D photographs of the peoples' feet, the attributes of different people whose feet were used to generate the structured 3D models, and the pressure maps that are recorded for the feet by (physical) foot scanners. The training data therefore includes a correspondence between the structured 3D model, the personal attributes, and the pressure map of the feet for each person. This training data is used to train the foot pressure estimation DLN to produce pressure maps for peoples' feet from a structured 3D model (obtained from a series of 2D images) and personal attributes, as detailed herein.

In one embodiment, a computer-implemented method for generating a pressure map of an object is disclosed, the computer-implemented method executable by a hardware processor, the method comprising receiving a plurality of 2-dimensional (2D) images of the object, wherein the plurality of 2D images capture the object from different angles, receiving one or more input parameters, the input parameters comprising at least one attribute related to the object, constructing a structured 3-dimensional (3D) model of the object from the plurality of 2D images, and generating the pressure map of the object from the structured 3D model and the input parameters using a pressure estimation deep learning network (DLN), wherein the pressure estimation DLN is trained to generate pressure maps of objects from a given structured 3D model and given parameters of a given object.

In one embodiment, constructing the structured 3D model of the object from the plurality of 2D images comprises generating a scaled unstructured 3D mesh of the object from the plurality of 2D images using a photogrammetry process and a scale factor, wherein the scaled unstructured 3D mesh is utilized to generate the structured 3D model.

In one embodiment, constructing the structured 3D model of the object from the plurality of 2D images further comprises generating the structured 3D model from an annotated scaled unstructured 3D mesh by morphing an annotated structured base 3D mesh to match the annotated scaled unstructured 3D mesh (i.e., through retopology).

In one embodiment, constructing the structured 3D model of the object from the plurality of 2D images further comprises utilizing a 3D keypoint DLN to generate the annotated scaled unstructured 3D mesh of the object from the scaled unstructured 3D mesh of the object, wherein the annotated scaled unstructured 3D mesh is utilized to generate the structured 3D model.

In one embodiment, the 3D keypoint DLN is based on a PointNet.

In one embodiment, constructing the structured 3D model of the object from the plurality of 2D images further comprises utilizing a 2D keypoint DLN to extract one or more keypoints from the plurality of 2D images, wherein the one or more keypoints are used to generate the annotated unstructured 3D mesh in order to generate the structured 3D model.

In one embodiment, constructing the structured 3D model of the object from the plurality of 2D images further comprises projecting the one or more keypoints onto the scaled unstructured 3D mesh of the object to generate the annotated scaled unstructured 3D mesh, wherein the annotated scaled unstructured 3D mesh is utilized to generate the structured 3D model.

In one embodiment, the 2D keypoint DLN is selected from the group consisting of a stacked hourglass network and a high-resolution network (HRNet).

In one embodiment, generating the pressure map of the object from the structured 3D model and the input parameters further comprises generating a density map by projecting the structured 3D model onto a surface, wherein the density map is utilized to generate the pressure map.

In one embodiment, the pressure estimation DLN is a modified vector quantized-variational auto-encoder (VQ-VAE), wherein the density map is utilized as input to the modified VQ-VAE to generate the pressure map, and wherein the modified VQ-VAE is trained to generate a given pressure map from a given density map and one or more given input parameters.

In one embodiment, the one or more input parameters comprise at least a scale factor, and wherein the scale factor is used to scale the structured 3D model to real-world coordinates.

In one embodiment, the method further comprises providing instructions to manufacture a 3D product from the structured 3D model utilizing 3D measurements extracted from the structured 3D model.

In one embodiment, the object is a body part (e.g., a foot or a hand).

In one embodiment, the pressure estimation DLN is trained on training data comprising structured 3D models from a 3D scanner and corresponding pressure maps from an object pressure sensor.

In one embodiment, the structured 3D model comprises at least one 3D model of a nude human foot without footwear or any other covering.

In one embodiment, the pressure map prediction deep learning network (DLN) comprises a convolutional neural network (CNN). In one embodiment, the deep learning network (DLN) further comprises a pyramid pooling module.

In one embodiment, the method further comprises post-processing the training data set before providing the training data set to train the deep learning network (DLN).

In various embodiments, a computer program product is disclosed. The computer program may be used for generating a pressure map of an object from a series of 2D images of the object, and may include a computer readable storage medium having program instructions, or program code, embodied therewith, the program instructions executable by a processor to cause the processor to perform steps to the aforementioned steps.

In various embodiments, a system is described, including a memory that stores computer-executable instructions; a hardware processor, operably coupled to the memory, and that executes the computer-executable instructions stored in the memory, wherein the computer-executable instructions may include instructions communicatively coupled with the processor that execute the aforementioned steps.

In another embodiment, the present invention is a non-transitory, computer-readable storage medium storing executable instructions, which when executed by a processor, causes the processor to perform a process for generating pressure maps, the instructions causing the processor to perform the aforementioned steps.

In another embodiment, the present invention is a system for pressure map prediction using a 2D phone camera, the system comprising a user device having a 2D camera, a processor, a display, a first memory; a server comprising a second memory and a data repository; a telecommunications-link between said user device and said server; and a plurality of computer codes embodied on said first and second memory of said user-device and said server, said plurality of computer codes which when executed causes said server and said user-device to execute a process comprising the aforementioned steps.

In yet another embodiment, the present invention is a computerized server comprising at least one processor, memory, and a plurality of computer codes embodied on said memory, said plurality of computer codes which when executed causes said processor to execute a process comprising the aforementioned steps. Other aspects and embodiments of the present invention include the methods, processes, and algorithms comprising the steps described herein, and also include the processes and modes of operation of the systems and servers described herein.

Yet other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings, in which:

FIG. 5 shows examples of the 2D photographs and 3D models constructed from the 2D photographs by a photogrammetry process in accordance with an embodiment.

FIGS. 13A, 13B, 14A, 14B, and 15 are illustrative diagrams of a use case of the present invention in which a mobile device with a single camera and an AR guided scan application is used as an interface for pressure map prediction, showing mobile graphical user interfaces (GUIs) through which some embodiments of the present invention have been implemented.

DETAILED DESCRIPTION OF THE INVENTION

Overview

Figure 1A:
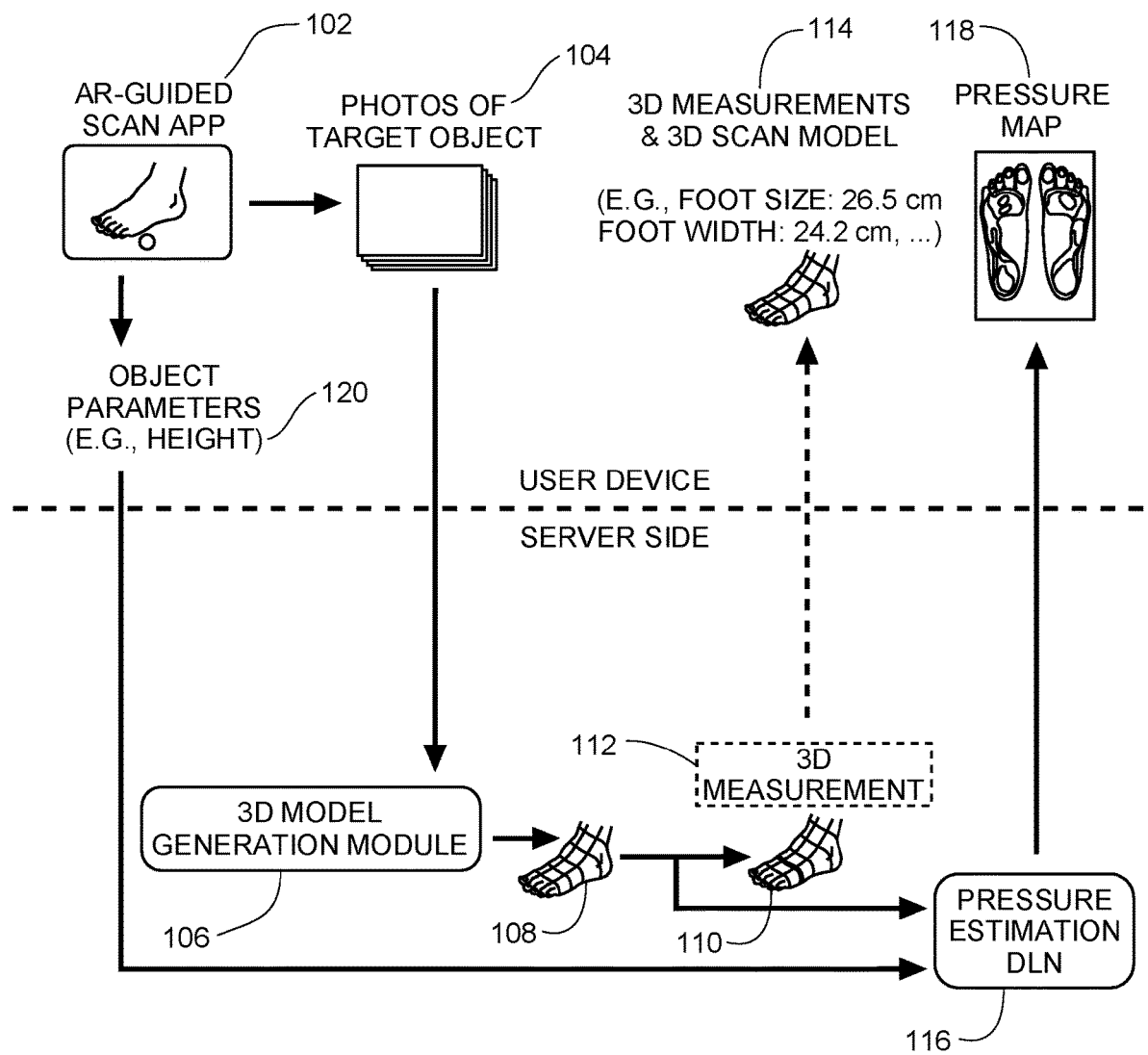
FIG. 1A shows an overview schematic diagram of a pressure map prediction system in accordance with one embodiment of the present invention.

With reference to the figures provided, embodiments of the present invention are now described in detail.

In the following description, for purposes of explanation, numerous specific details are set forth in order to provide a thorough understanding of the invention. It will be apparent, however, to one skilled in the art that the invention can be practiced without these specific details. In other instances, structures, devices, activities, and methods are shown using schematics, use cases, and/or flow diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Pressure maps that represent the pressure profiles showing points of higher and lower pressures when two surfaces are in contact are very useful in designing and manufacturing of products. Currently available pressure mapping technologies involve the use of hardware such as sensors, scanners, and software to analyze the collected data and generate the pressure maps. As a result, it is a requirement for these pressure mapping systems that the surfaces under test be brought into physical contact with each other in order to collect the pressure profiles between the surfaces. Bringing the objects whose surfaces are to be tested for pressure profile data into physical proximity may not always be feasible due to size or distance issues, or health reasons in case of patients in healthcare/medical device applications. The pressure map prediction system disclosed herein mitigates the need for physical proximity between surfaces under test by enabling generation of pressure maps based on 3D models of the objects reconstructed from a series of 2D images. As a result, not only is the travel minimized for users to get their customized products or medical devices, but also the use of sensor or scanner hardware is reduced, or eliminated entirely, reducing friction points for users of the system.

Instead, advanced computer vision algorithms combined with deep-learning techniques may be used to generate accurate pressure maps of objects from photos provided from a simple 2D mobile device camera. In the present disclosure, the term "2D mobile device camera" is used to represent any traditional cameras embedded in, or connected to, computing devices, such as smart phones, tablets, laptops, or desktops. The 2D images captured by such cameras are termed "2D photos", "images", or "photographs". One difficulty with implementing deep learning networks for pressure map generation from 2D photos is that training data sets are required to train the deep learning networks. In one embodiment, the present invention also provides methodologies for training the deep learning networks to predict or generate pressure maps from 2D images.

Generating Pressure Maps of Objects from 2D Images

FIG. 1A shows an overview schematic diagram of a pressure map prediction system in accordance with one embodiment of the present invention. In one embodiment, an augmented reality (AR) guided scan application 102 assists a user with taking a series of photos 104 of the object (e.g., a human foot). Object-related parameters 120 (e.g., object or user height) are also collected by the AR-guided scan app 102. The photos 104 and object parameters 120 are sent to a server, where a 3D model generation module 106 comprising various processes such as photogrammetry, retopology, and one or more Deep Learning Networks (DLNs), is used to construct a structured 3D model 108 of the object from the photos 104. From the structured 3D model 110, any number of measurements may be performed, for example, using a script 112, to obtain any desired measurement(s) 114 of the object from the structured 3D model. Furthermore, from the structured 3D model, and one or more object parameters 120, a pressure estimation Deep Learning Network (DLN) 116 located on the server predicts a pressure map 118 of the object, as described in greater detail below. Finally, the resulting pressure map 118, measurement(s), and 3D scan model 114 may be sent to the user device.

Figure 1B:
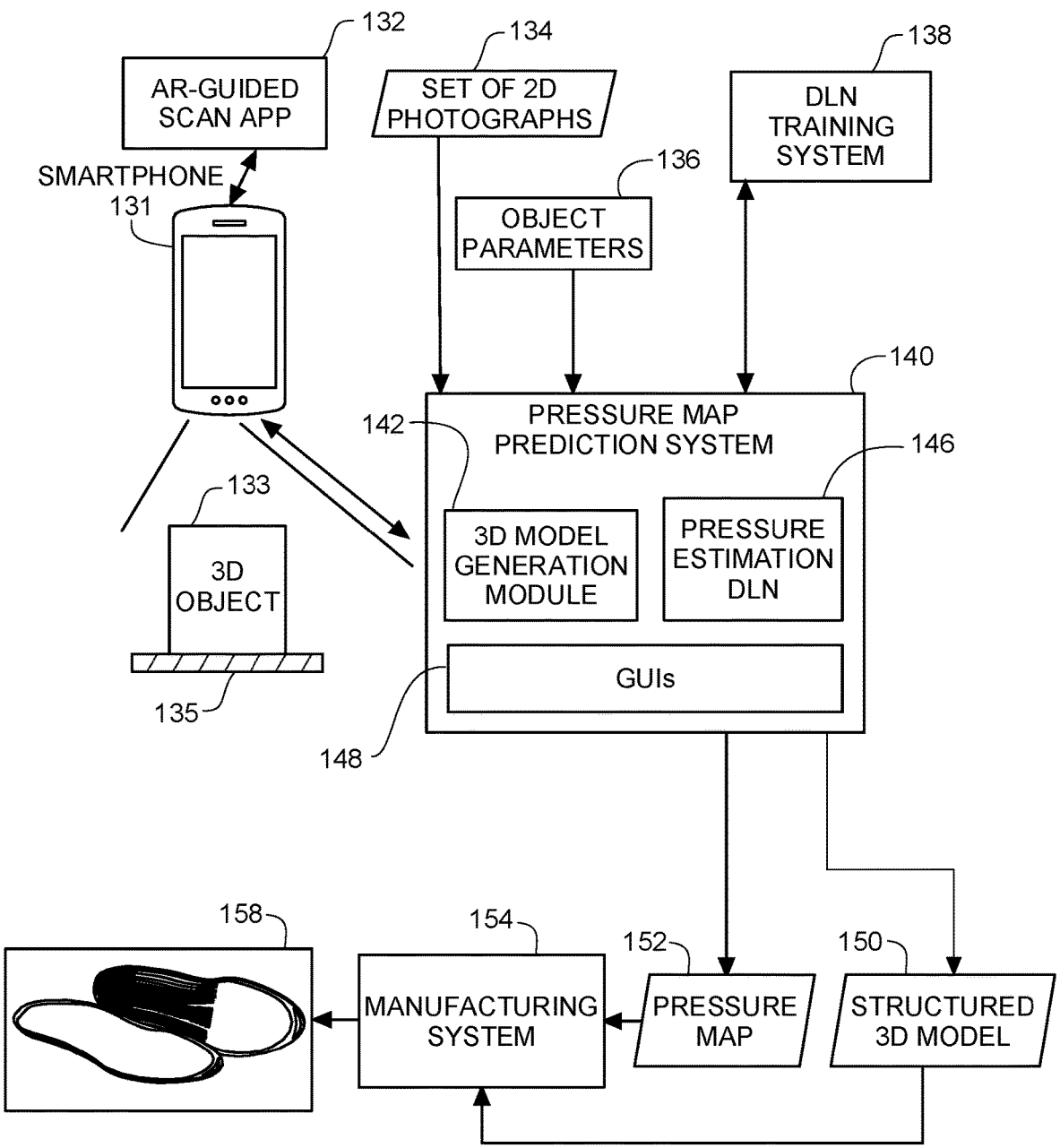
FIG. 1B shows another overview schematic diagram of a pressure map prediction system in accordance with another embodiment of the present invention.

FIG. 1B shows a detailed schematic diagram of a pressure map prediction system in accordance with another embodiment of the present invention. The pressure map prediction system receives a series of 2D images 134, e.g., photographs of a real-word object 133 resting on a surface 135 for which a pressure map 152 is to be generated. A set of about 4-6 (or more) photographs 134 of the object 133 can be taken from different angles from various sides of the object 133 so that the object 133 is captured from various directions in the series of photographs 134. A camera attached to a smartphone 131, a tablet device, or other imaging hardware can be used to capture the series of 2D photographs 134. In an embodiment, the smartphone 131 can execute an augmented reality (AR) guided scanning application 102, 132 to assist a user with accurately capturing the photographs 134 of the object 133. Generally, a series of 40-60 photographs may be required for reconstructing a 3D model of the object 133 using traditional photogrammetry processes. However, the AR guided scanning application 132 can be configured programmatically to identify the angles, heights, and direction from which the object 133 is to be photographed in order to secure maximum coverage. Accordingly, the AR guided scanning application 132 can guide the user via text or voice prompts to place the smartphone 131 at specific heights, in particular directions, and at particular angles to best capture the object 133 for the 3D model 150 construction. Through the use of the AR guided scanning application 132, and the one or more Deep Learning Networks (DLNs) comprised within the pressure map prediction system 140, the number of photographs required may be reduced from 40-60 to about 4-6 photos, in one embodiment of the invention. The AR guided scanning application 132 can guide a user imaging an object (e.g., a foot) about the background requirements, the object positions, the distances, and the angles for capturing each of the series of 2D photographs 134. The AR guided scanning application 132 can be configured to provide these instructions based on the category of the object selected by the user, as objects belonging to different object categories can be processed by the pressure map prediction system 140. In another embodiment, the photos or parameters may be obtained from a database which is populated with the series of 2D photos 134.

The AR guided scanning application 132 can also require a user generating the series of photographs 134 to additionally enter certain object parameters 136. The object parameters 136 to be provided by the user can depend on the object 133 being imaged for which the pressure map 152 is to be predicted. In an example, the object parameters 136 can include not only the attributes of the object 133 being imaged but also the attributes of a larger body of which the object 133 may be only a portion. In an example, the user may be required to specifically identify the object 133 being imaged so that the AR guided scanning application 132 can correspondingly retrieve the object parameters 136. For example, if the object 133 being imaged is a person's foot, then the object parameters 136 can include the person's attributes such as, but not limited to, the height, weight, body mass index (BMI), racial profile, gender, etc.

The series of photographs 134 and object parameters 136 are provided to a pressure map prediction system 140 utilizing a 3D model generation module 142 and a pressure estimation Deep Learning Network (DLN) 146 which reconstructs a virtual structured 3D model 150 of the object 133 from the series of photographs 134. The 3D model generation module 142 executes a reconstruction of the structured 3D model 150 using photogrammetry, a keypoint DLN, and topology transfer (i.e., retopology or morphing), as described below. The keypoint DLN is a neural network that is trained to generate 2D or 3D keypoints that are necessary for the construction of the structured 3D model 150, as explained in greater detail in relation to FIGS. 2A, 2B, and 8. The topology transfer step uses the keypoints to morph a scanned base 3D mesh into the structured 3D model 150. Note that a measurement script can extract pre-defined object measurements from the structured 3D model of the object 150.

The structured 3D model 152 of the object 133 is now provided to an object pressure estimation DLN 146, along with the object parameters 136. The object pressure estimation DLN 146 is trained by a DLN training system 138 to predict or generate the pressure map 152 of the object 133 with respect to a surface 135, based on a structured 3D model of the object 133. The object pressure estimation DLN 146 architecture is described in greater detail in relation to FIG. 10. The pressure map 152 provides a visual representation of the profile of the pressures exerted by the object 133 in contact with the surface 135. Higher pressure areas are indicated by certain colors or color intensities, while other different colors or color intensities can be used to indicate lower pressure areas. In an embodiment, the pressure map 152 can be displayed on a display of a computing device. In an embodiment, the pressure map 152 of the object 133 can be further transmitted to other systems for the execution of downstream processes, for example, a custom manufacturing process.

The object pressure estimation DLN 146 can be trained to generate the pressure maps for a given object category by the DLN training system 138 as detailed further herein. Therefore, different object pressure estimation DLNs can be trained to produce pressure maps for different objects in response to receiving the structured 3D models and object parameters of the particular object category. The pressure maps are therefore obtained from a trained DLN without the necessity for scanning or sensor hardware, and without the need for the object to be in physical proximity to such hardware. The pressure maps generated by the object pressure estimation DLN 146 can be displayed via GUIs 148 associated with the pressure map prediction system 140. However, displaying pressure maps may not always be needed as the pressure maps can be further transmitted for execution of further downstream processes, such as a custom manufacturing process.

Based on the pressure maps of various object categories, various applications are made possible. One such application includes production of customized footwear, clothing, or accessories. In an embodiment, the object 133 being imaged for the purpose of prediction of the pressure map can pertain to a person's body part, such as a person's foot. The AR guided scanning application 132 can be used to generate the series of 2D photographs of a person's naked foot. A structured 3D model 152 of the foot is reconstructed by the 3D model generation module 142 from the series of 2D photographs 134. The 3D model along with the person's parameters 136 such as the height, weight, BMI, racial profile, gender, etc. are collected from the AR guided scanning application 132. The object pressure estimation DLN 146 accesses the structured 3D model and the person's parameters and predicts the pressure map 152 of the person's foot. The pressure map 152 and retopologized structured 3D model 150 can be further accessed by a manufacturing system 154, such as a 3D printing system, which can print footwear or foot accessories, such as insoles 158, customized to the foot of the person.

Generating Object Measurements

In an example, the feet pressure map 152, in combination with the retopologized structured 3D model 150, enables obtaining the dimensions of the feet and the pressure profile of the feet. Along with length, the person's width, and the foot arch type (high, medium, or low), as well as pressure map 152, can be considered in manufacturing the insoles 158. In certain embodiments, Mask-Region Convolutional Neural Networks (R-CNN), which detects objects in an image, can be applied to determine the measurements of the feet from the foot pressure maps. Mask-RCNN based object segmentation, when applied to an isolated image of the foot, enables measuring the attributes of the feet in the foot pressure map. Various methods using, for example, a Python script based on the structured 3D models in virtual space can be implemented for obtaining the dimensions or the measurements of the object 133 from the structured 3D model 150. Alternatively, object measurement procedures can also be implemented using Regional Convolutional Neural Network (RCNN), Fast-RCNN, etc.

For feet measurement applications, the system considers feet dimensions and shapes in order to generate the insoles. Furthermore, the pressure map of a person's foot provides a representation of the high pressure, medium pressure, and low pressure points of the person's foot. As a result, an insole customized to a person's foot pressure profile, in addition to their feet dimension and shape, can be manufactured.

Use of Artificial Intelligence (AI) Algorithms for Pressure Estimation

As noted, embodiments of devices and systems (and their various components) described herein can employ artificial intelligence (AI) to facilitate automating one or more features described herein (e.g., reconstructing the structured 3D model, predicting the pressure map, and the like). The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context, or can generate a probability distribution over states, for example. The determinations can be probabilistic; that is, a computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determinations.

For example, a classifier may map an input attribute vector, $z=(z_1, z_2, z_3, z_4, \ldots, z_n)$, to a confidence that the input belongs to a class, as by $f(z)=\text{confidence}(\text{class})$. Such classification may employ a probabilistic and/or statistical-based analysis (e.g., factoring into the analysis utilities and costs) to determinate an action to be automatically performed. Another example of a classifier that can be employed is a support vector machine (SVM). The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naive Bayes, Bayesian networks, decision trees, neural networks, fuzzy logic models, and/or probabilistic classification models providing different patterns of independence, can be employed. Classification as used herein also is inclusive of statistical regression that is utilized to develop models of priority.

Figure 2A:
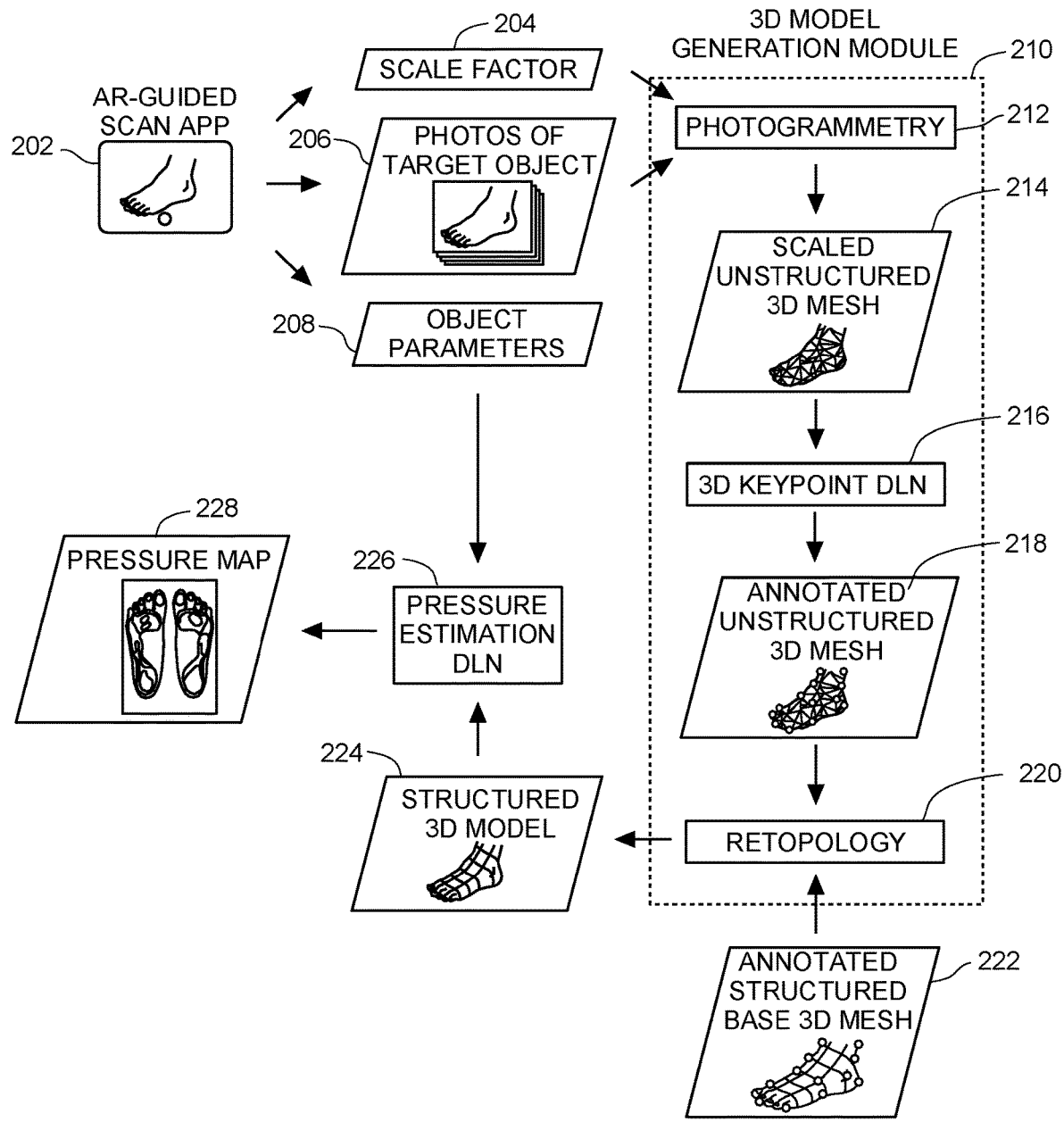
FIGS. 2A and 2B show detailed schematic diagrams of two illustrative processes for generating a pressure map from a series of 2D photographs of an object in accordance with exemplary embodiments of the present invention.
Figure 2B:
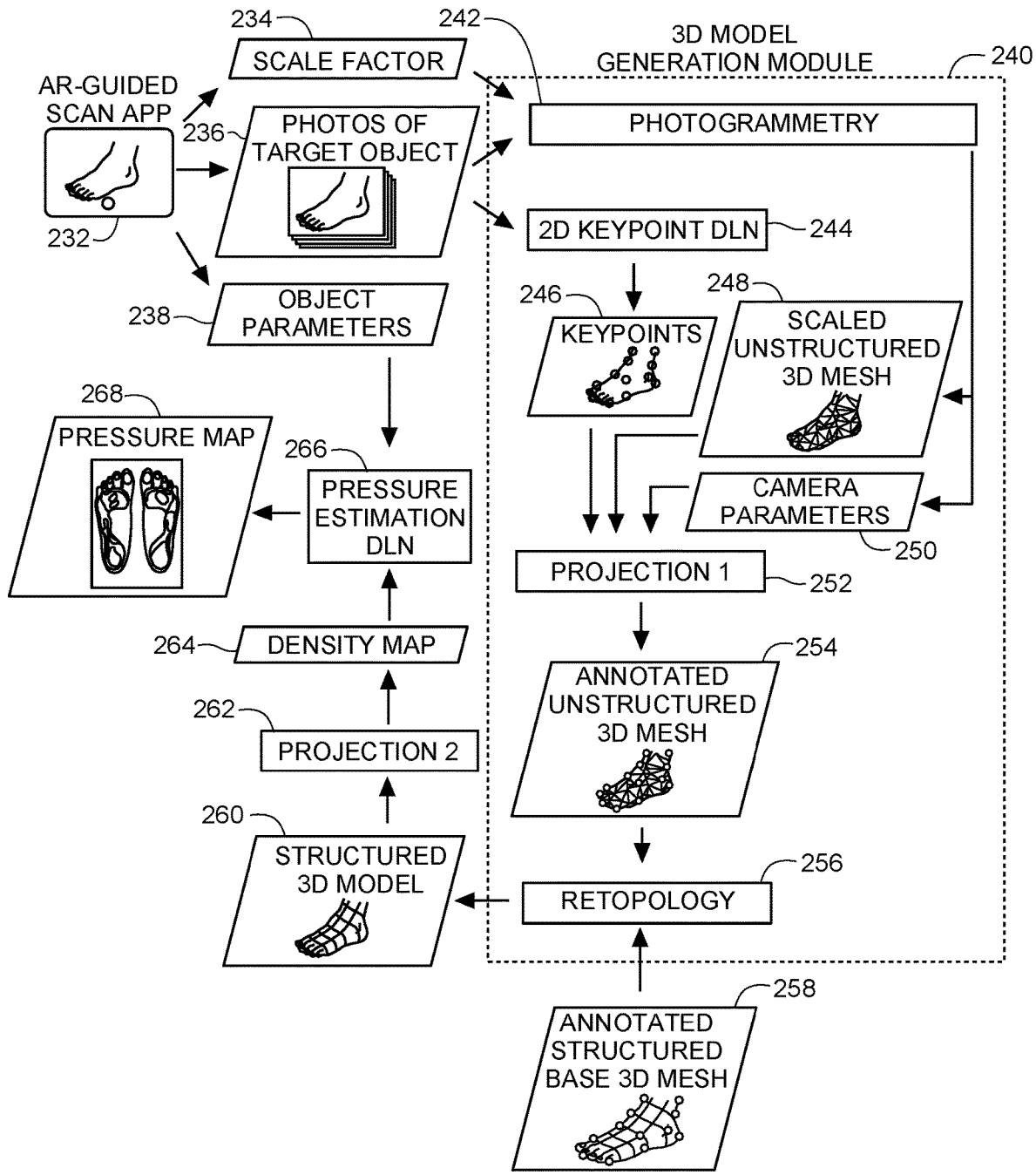

FIGS. 2A and 2B show detailed schematic diagrams of two illustrative processes for generating a pressure map from a series of 2D photographs of an object in accordance with exemplary embodiments of the present invention.

In FIG. 2A, an AR-guided application 202 is used as an interface to obtain photos 206 and parameters 208 of the target object. The AR app 202 also collects a scale factor for distance normalization purposes. The scale factor 204 represents normalization data to enable the conversion of dimensions of the object 133 or its background from pixel coordinates on the photos 206 to real world coordinates. In various embodiments, depth data from a sensor on a mobile computing device, an object parameter (e.g., object height), or a reference object of known size in the received photos, can be used as a scale factor 204 to scale from pixel coordinates to real-world coordinates. The scale factor 204 allows the scaling of the meshes within the 3D model generation module 210 to real-world dimensions. The photos 206 and scale factor 204 collected through the AR scan app 202 are sent to a 3D model generation module 210 to generate a structured 3D model 224 of the object.

Structured and unstructured meshes differ by their connectivity. An unstructured mesh has irregular connectivity between vertices, requiring the explicit listing of the way vertices make up individual mesh elements. Unstructured meshes therefore allow for irregular mesh elements but require the explicit storage of adjacent vertex relationships, leading to lower storage efficiency and lower resolution. A structured mesh, however, has regular connectivity between its vertices (i.e., mesh elements and vertex distances are predefined), leading to higher space and storage efficiency, and superior resolution.

In the embodiment described in FIG. 2A, the 3D model generation module 210 carries out three major operations: photogrammetry 212, 3D keypoint detection 216, and retopology 220. Photogrammetry 212 uses the input photos of the target object 206 and the scale factor 204 to generate a scaled unstructured mesh 214 representing the object in three dimensions. Photogrammetry 212 is described in detail below, in the context of FIG. 4. The scaled unstructured mesh 214 generated by the photogrammetry 212 process is then fed to a 3D keypoint DLN 216.

Keypoint annotation is the process of annotating the scaled unstructured mesh 214 by detecting keypoints within the mesh representation of the 3D object (e.g., on the object surface). The annotation of the unstructured 3D mesh is required as an initial stage in the generation of the structured 3D model. Annotation is the generation of annotation keypoints indicating salient features of the target object 133. Mesh annotations may be carried out through one or more annotation DLN modules that have been trained on a specific object type (e.g., a specific body part). In some embodiments, for example, the segmentation of the object from the background may be carried out by a separate DLN.

The keypoint detection process falls under the broad category of landmark detection. Landmark detection is a category of computer vision applications where DLNs are commonly used. Landmark detection denotes the identification of salient features in 2D or 3D imaging data and is widely used for purposes of localization, object recognition, etc. Various DLNs such as PointNet, FeedForward Neural Network (FFNN), Faster Regional Convolutional Neural Network (Faster R-CNN), and various other Convolutional Neural Network (CNNs) were designed for landmark detection. The 3D keypoint DLN 216 can be based on any 3D landmark detection machine learning algorithm, such as a PointNet.

PointNets are highly efficient DLNs that are applied in 3D semantic parsing, part segmentation, as well as classification. PointNets are designed to process point clouds directly, hence allowing effective 3D landmark detection. PoitnNets also avoid unnecessary transformations of the unstructured 3D mesh input. In one embodiment, the PointNet algorithm is implemented as described in Charles R. Qi, et al., "PointNet: Deep Learning on Point Sets for 3D Classification and Segmentation," CVPR 2017, Nov. 9, 2017, available at arXiv: 1612.00593, which is hereby incorporated by reference in its entirety herein as if fully set forth herein. PointNets are only illustrative DLN algorithms that are within the scope of the present invention, and the present invention is not limited to the use of PointNets. Other DLN algorithms are also within the scope of the present invention. For example, in one embodiment of the present invention, a convolutional neural network (CNN) is utilized as a 3D keypoint DLN 216 to extract object keypoints and to annotate meshes.

To carry out 3D keypoint annotation, the 3D keypoint DLN must be trained beforehand using training data sets comprising object meshes and corresponding keypoint annotations. Keypoint annotation DLNs can be trained to detect keypoints for a specific type of object. In some embodiments, segmentation (i.e., the separation of the object from its background) and annotation can be carried out through different DLNs. The 3D keypoint annotation DLN produces an annotated unstructured 3D mesh 218.

The retopology process 220 uses the annotated unstructured 3D mesh 218 alongside an annotated structured base 3D mesh 222 to generate a scaled structured 3D model 224. Retopology 220 is a morphing process that deforms the shape of an existing structured and annotated base 3D mesh 222 of the object into a structured 3D model 224 of the target object 133 so that its keypoints match the keypoints detected on the object 133 by the 3D keypoint DLN 216 (and represented by the annotated unstructured 3D mesh 218). Retopology may also operate on the mesh surface or projected two-dimensional contour, as discussed in the context of FIG. 9. The base 3D mesh 222 is a raw 3D mesh representation of the object that is stored on a server or within the device. The retopology process 220 can access a library of 3D base meshes containing at least one base 3D mesh 222 in the category of the target object 133. In one embodiment, the base 3D meshes in the library are structured and pre-annotated. The morphing of the base 3D mesh therefore produces a scaled and structured 3D mesh representation 224 of the object. Retopology is further discussed in more detail in the context of FIG. 9.

The structured 3D model 224 generated by the 3D model generation module 210 is then input to a pressure estimation DLN 226, along with the object parameters 208, in order to generate the output pressure map 228 of the object 133. The pressure estimation DLN may use any suitable DLN algorithm. For example, the Vector Quantized-Variational Auto-Encoder (VQ-VAE) is a type of DLN that is particularly suitable to generate the pressure map 228, as discussed below. Naturally, VQ-VAEs are only illustrative DLN algorithms that are within the scope of the present invention, and the present invention is not limited to the use of VQ-VAEs. Other DLN algorithms are also within the scope of the present invention.

Figure 7:
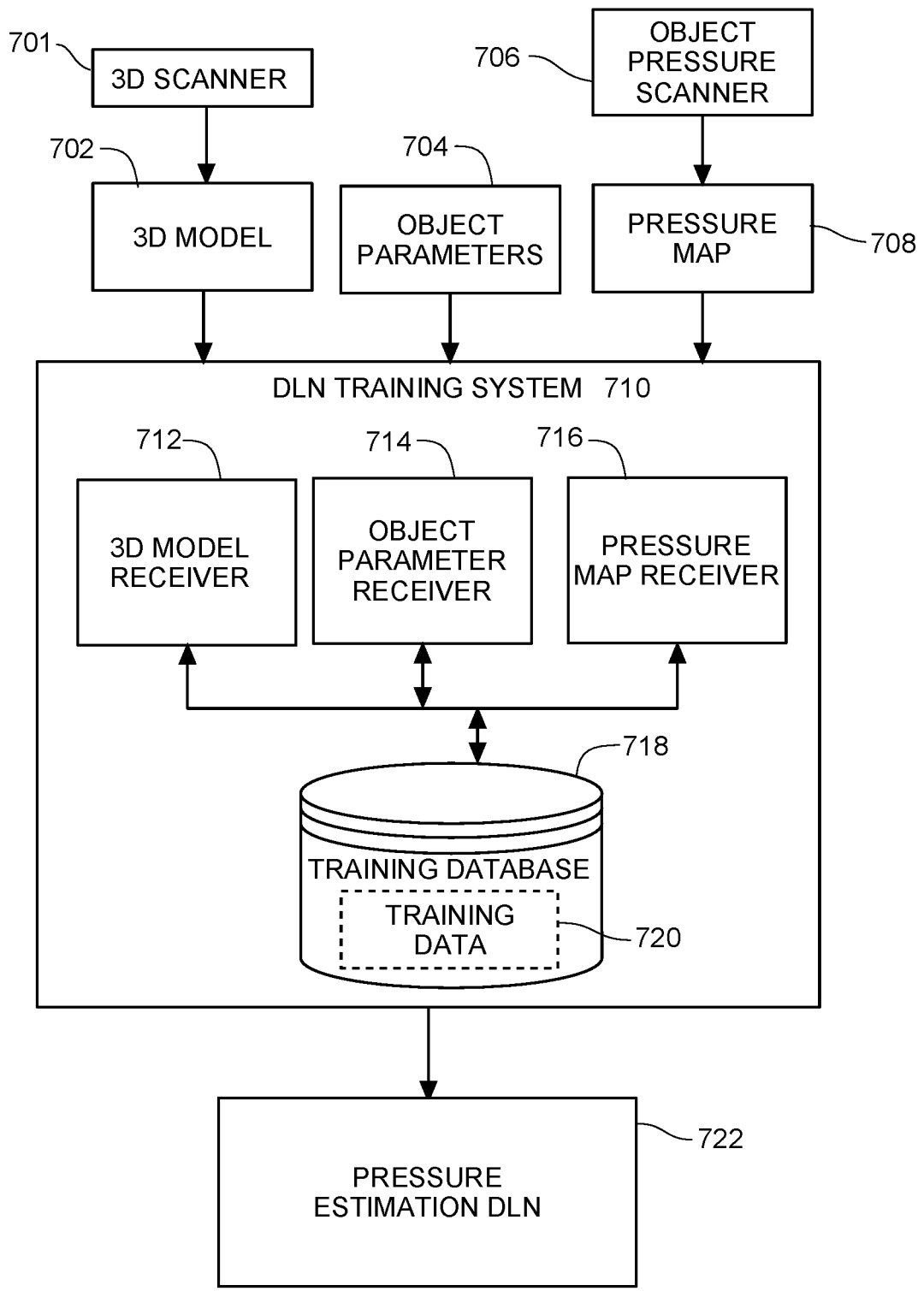
FIG. 7 shows a block diagram of a DLN training system for training an object pressure estimation DLN via supervised learning in accordance with one embodiment.

To carry out pressure estimation, the pressure estimation DLN 226 must be trained beforehand using training data sets comprising structured 3D models of objects and corresponding pressure maps, as described in detail in FIG. 7. Pressure estimation DLNs can be trained to generate pressure maps for a specific type of object (e.g., human foot).

FIG. 2B depicts different embodiments of the present invention, where a 2D keypoint DLN 244 is used instead of a 3D keypoint DLN 216 and the pressure estimation DLN 266 requires a density map 264 to generate the pressure map 268. In FIG. 2B, an AR-guided application 232 is used as an interface to obtain photos 236 and parameters 238 of the target object. The AR app 232 also collects a scale factor for distance normalization purposes. The scale factor 234 represents normalization data to enables the conversion of dimensions of the object 133 or its background from pixel coordinates on the photos 236 to real world coordinates. The scale factor 234 hence allows the scaling of the meshes within the 3D model generation module 240 to real-world dimensions. The photos 236 and scale factor 234 collected through the AR scan app 232 are sent to a 3D model generation module 240 to generate a structured 3D model 260 of the object.

In the embodiment described in FIG. 2B, the 3D model generation module 240 carries out four major operations: photogrammetry 242, 2D keypoint detection 244, keypoint projection 252 (denoted "projection 1"), and retopology 256. As for FIG. 2A, photogrammetry 242 uses the input photos of the target object 236 and the scale factor 234 to generate a scaled unstructured mesh 248 representing the object in three dimensions. However, the photogrammetry process 242 also generates camera parameters 250 necessary for accurate keypoint projection 252. Camera parameters 252 may include position parameters (e.g., camera location and rotation) as well as internal parameters such as the camera's focal length, lens distortion, sampling (pixel size), or imaging size (i.e., size of the digital sensor's imaging area). Photogrammetry 242 is described in detail below, in the context of FIG. 4.

In the embodiment of FIG. 2B, the 3D model generation module 240 uses a 2D keypoint DLN 244 to generate keypoints 246 from the input photos 236. In this context, 2D keypoint detection is the process of detecting and extracting keypoints 246 from the 2D photos 236. The generated keypoints indicate salient features of the target object 133 on the 2D photos 236. In the keypoint projection step 252 (projection 1), the generated keypoints 246 are projected onto the scaled unstructured 3D mesh 248, where the camera parameters 250 are used to accurately determine the location of the keypoints 246 in 3D space. The projection step 252 therefore combines the keypoints 246 with the scaled unstructured 3D mesh 248 to generate an annotated unstructured 3D mesh 254.

Keypoint generation may be carried out through one or more 2D keypoint DLN modules that have been trained on a specific object type (e.g., human foot). In some embodiments, the segmentation of the object from the background may be carried out by a separate DLN. The 2D keypoint generation process also falls under the category of landmark detection, as discussed above. Various landmark DLNs, such as the Stacked Hourglass Convolutional Neural Network (CNN), HRNet, FeedForward Neural Network (FFNN), Faster Regional Convolutional Neural Network (Faster R-CNN), and other CNNs, may be used to build a 2D keypoint DLN. An exemplary architecture of a Stacked Hourglass CNN is discussed in the context of FIG. 8.

To carry out 2D keypoint annotation, the 2D keypoint DLN must be trained beforehand using training data sets comprising object photos and corresponding keypoints. 2D keypoint DLNs can be trained to detect keypoints for a specific type of object. In some embodiments, segmentation (i.e., the separation of the object from its background) and annotation can be carried out through different DLNs, as mentioned above.

As is the case in the embodiment of FIG. 2A, the keypoint projection 252 step (projection 1) produces an annotated unstructured 3D mesh 254. Similarly, the retopology process 256 uses the annotated unstructured 3D mesh 254 alongside an annotated structured base 3D mesh 258 to generate a scaled structured 3D model 260. Retopology is further discussed in more detail in the context of FIG. 9.

In FIG. 2B, the transition from a structured 2D model 260 to a pressure map 268 uses an embodiment that is different from that of FIG. 2A. The structured 3D model 260 generated by the 3D model generation module 240 is first converted to a density map 264 through a second projection process 262 (projection 2). The density map 264 is then input to a pressure estimation DLN 266 to generate the pressure map of the target object 133. The density map 264 is a 2D representation of the volume of the target object 133 as projected on a reference surface. In one embodiment, it is generated by projecting the distance between the closest and farthest points of the structured 3D model 260 onto the reference surface, so that each point on the density map represents the thickness of the object along the axis of projection.

The pressure estimation DLN 266 uses the density map 264 and the object parameters 238 to generate the output pressure map 268 of the object 133. The pressure estimation DLN may use any suitable DLN method. A VQ-VAE algorithm that is modified for the purpose of generating pressure maps from density maps and object parameters is discussed in FIG. 10.

The DLN algorithms listed above for the various DLN applications disclosed herein (e.g., Stacked Hourglass, HRHNet, VQ-VAE, etc.) are only illustrative algorithms that are within the scope of the present invention, and the present invention is not limited to the use of the listed DLN algorithms. Other DLN algorithms are also within the scope of the present invention. Moreover, other machine learning (ML) methods may be used instead of or in combination with the various listed DLN algorithms. Other ML algorithms including, but not limited to, regressors, nearest neighbor algorithms, decision trees, support vector machines (SVM), Adaboost, Bayesian networks, fuzzy logic models, evolutionary algorithms, and so forth, are hence within the scope of the present invention.

Figure 3:
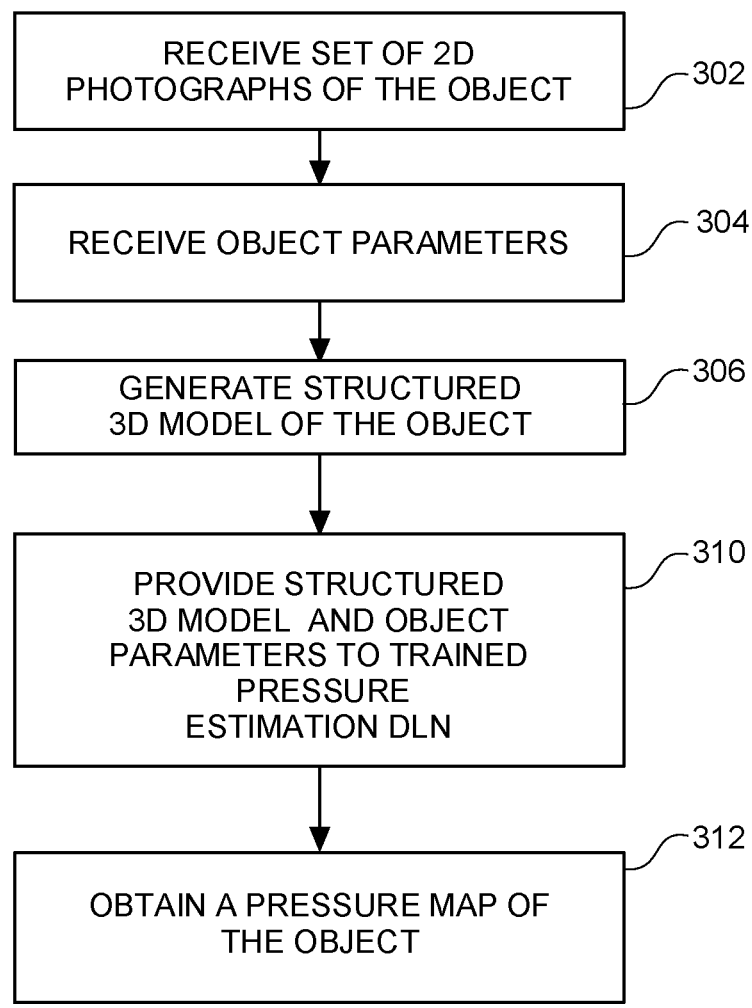
FIG. 3 shows a flowchart illustrating a process for generating a pressure map from a series of 2D photographs of an object in accordance with one embodiment of the present invention.

FIG. 3 shows a flowchart of a process for generating a pressure map from a series of 2D photographs of an object in accordance with an embodiment. At step 302, a series of 2D photographs 134, 206, 236 are obtained. Each photograph of the series of photographs can be approximately 4-5 megapixels, showing the object 133 in its entirety, without defects such as blurring, etc., in order to be useful for the generation of the structured 3D model 150, 224, 260. Generally, photogrammetry processes require 40-60 photographs of the object 133 from different angles. However, in one embodiment of the invention, using the AR guided scanning application 132, 202, 232 along with the keypoint Deep Learning Networks (DLNs) 216, 244, one can reduce the number of photographs to a mere 4-6 photographs, as the photographer recording the photographic data can be guided to the exact angles and distances that can give optimal coverage of the object 133 for the structured 3D model construction in order to provide sufficient information for the 3D model generation module 210, 240 to reconstruct the 3D model.

At step 304, the object parameters 136, 208, 238 are also received, for example, via the AR guided scanning application 132, 202, 232. As mentioned above, the user recording the photographic data can be required to enter an object category so that a set of object parameters can be selected for collection. Again, the object parameters 136, 208, 238 may be object attributes, where the object 133 is complete and not part of a larger body, and is therefore being photographed in its entirety. However, if the object 133 is a portion of a larger body, e.g., a person's hand or foot, then the object parameters 136, 208, 238 can also include the characteristics of the larger body, such as the person's weight, height, etc.

The series of 2D photographs 134, 206, 236 and the object parameters 136, 208, 238 are provided to the 3D model generation module 142, 210, 240 which constructs a structured 3D model 150, 224, 260 of the object 133 from the series of photographs 134, 206, 236 at step 306, as discussed in the context of FIGS. 2A and 2B.

The structured 3D model 150, 224, 260 and the object parameters 136, 208, 238 are provided, directly (FIG. 2A) or indirectly (FIG. 2B), to the object pressure estimation DLN 146, 226, 266 at step 310. The object pressure estimation DLN 146, 226, 266, which is trained to estimate the pressure at each point within the area of contact between the object 133 and a surface 135, predicts the pressure map 152, 228, 268 of the object 133 at step 312. The pressure maps thus generated can be further accessed for analysis purposes or for enabling downstream manufacturing processes. The data regarding the pressure map 152, 228, 268 can be directly exported to an external system, such as a manufacturing system 154 without a visible GUI output, in one embodiment. In another embodiment, a visible output in the form of the pressure map displayed on one or more GUIs on one or more computing devices, may be produced (e.g., FIG. 15).

Illustrative Photogrammetry Process

Figure 4:
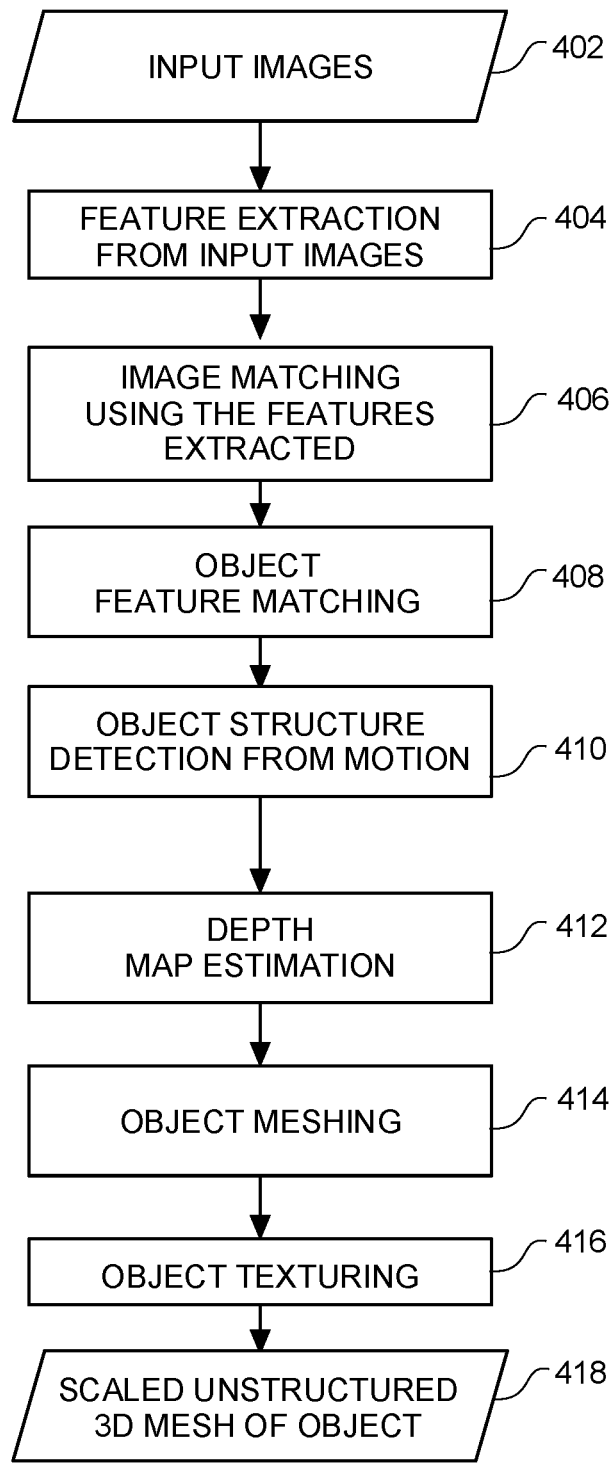
FIG. 4 shows a flowchart that details an example of a method for constructing a scaled unstructured 3D mesh from 2D photographs using one embodiment of a photogrammetry process.

FIG. 4 shows a flowchart that details an example of a method for constructing a scaled unstructured 3D mesh 214, 248 from 2D photographs 206, 236. Various algorithms are within the scope of the present invention for constructing scaled unstructured 3D meshes from the 2D photographs. Discussed below, by way of illustration and not limitation, are steps implemented by one embodiment of the present invention for scaled unstructured 3D mesh generation. Implementation of other algorithms may involve different steps or processes in the construction of a scaled unstructured 3D mesh 214, 248. Further steps for the generation of a structured 3D model of an object are disclosed in relation to FIGS. 8, 9, and 10.

The photogrammetry process initially extracts features from the 2D photographs 402, 206, 236 at step 404. As a result, distinctive groups of pixels that are invariant to changing camera view points in the series of 2D photographs 402, 206, 236 are extracted. Feature detection methods such as the Scale-invariant feature transform (SIFT) algorithm may be used. SIFT initially enables extraction of discriminative patches in a first image of the series of 2D photographs 402, 206, 236 that can be compared to discriminative patches of a second image in the series of 2D photographs 402, 206, 236 irrespective of rotation, translation, and scale. In this methodology, SIFT invariance can be used to deal with the image transformations occurring when the viewpoints are changing during image acquisition. In an example, a post-filtering step can be used to limit the number of extracted features.

At step 406, an image matching process is executed in order to identify the photographs that capture the same areas of the object 133. A vocabulary tree approach may be employed to generate image descriptors. The distance between the image descriptors is then computed in order to match the photographs showing the same portions of the object.

At step 408, the features between candidate image subsets, e.g., image pairs identified at 406, are matched. In an example, photometric matches between the set of descriptors from two or more input images may be performed. For example, for each feature in an input image I, a list of candidate matching features are obtained from an image II. Again, feature descriptors generated at step 406 can be employed for feature matching between image pairs. Processes such as Approximate Nearest Neighbor (ANN) can be employed for the feature matching.

At step 410, the geometric relationship behind the observations provided by the input images is analyzed, and the rigid scene structure (3D points) with the pose (position and orientation) and internal calibration of all cameras is inferred. An initial two-view reconstruction is first computed that is iteratively extended by adding new views.

For each of the cameras that have been resolved in step 410, the depth value of each pixel is retrieved at 412. Various methodologies such as, Block Matching, Semi-Global Matching (SGM), or ADCensus can be employed for the depth map estimation. The depth maps for each of the 2D photographs 402, 206, 236 can be computed independently and in parallel. A filtering step can ensure consistency between multiple cameras. A scale factor 204, 234 input can be used in steps 412 or 414, hence scaling the 3D representation of the object generated from the input images 402.

At the meshing step 414, a dense geometric surface representation of the scene (including the object 133) is created. All the depth maps are initially combined into a global octree where compatible depth values are merged into the octree cells. A complex voting procedure, e.g., 3D Delaunay tetrahedralization, is then executed to compute weights on cells and weights on facets connecting the cells. The resulting volume is then optimally cut by employing procedures like Graph Cut Max-Flow. This cut represents the extracted mesh surface. Other filtering procedures can be applied on the mesh to remove local artefacts and the mesh can also be simplified to reduce unnecessary vertices.

The mesh created at step 414 is textured at step 416. If the mesh has no associated "UV," the photogrammetry process can compute automatic "UV" maps. In this instance, the letters "U" and "V" denote the axes of the 2D texture. For each triangle, the visibility information associated with each vertex is then used to retrieve the texture candidates. The cameras without a good angle to the surface are filtered to favor fronto-parallel cameras and the pixel values are then averaged.

Each of the processes described above thus creates intermediate files. For example, the meshing process 414 creates an object file (e.g., "mesh.obj"). However, the end result is a texture map in the form of a textured "mesh.obj" which is of the object type. The background or other extraneous artefacts which are captured can be deleted, resulting in a scaled unstructured 3D mesh of the object 418. While the photogrammetry process can include a separate GUI for displaying the visual output at each step of the scaled unstructured 3D object mesh 418 creation process, a GUI is not needed in all scenarios. While high resolution textual maps, or 3D meshes, are generally created with default settings in the photogrammetry process, these high-resolution maps can be further processed using extracted keypoints 218, 246 and retopology 220, 256 to create structured texture maps (e.g., structured 3D models 150, 224, 260) of lower resolutions for real-time applications.

FIG. 5 illustrates 3D model generation 500, showing examples of 2D photographs 134, 206, 236 and structured 3D models 150, 224, 260 constructed from the 2D photographs by the 3D model generation module 142, 210, 240, in accordance with an embodiment. When photographs of a hand, e.g., image 502, is fed to the 3D model generation module 142, 210, 240, a structured 3D model of the hand as shown at 504 is generated. Similarly, when a series of photographs of a leg, such as the image 506 is fed to the 3D model generation module 142, 210, 240, a 3D model of the leg as shown at 506 is generated.

Custom In-Sole Manufacture Utilizing Generated Pressure Maps

Figure 6:
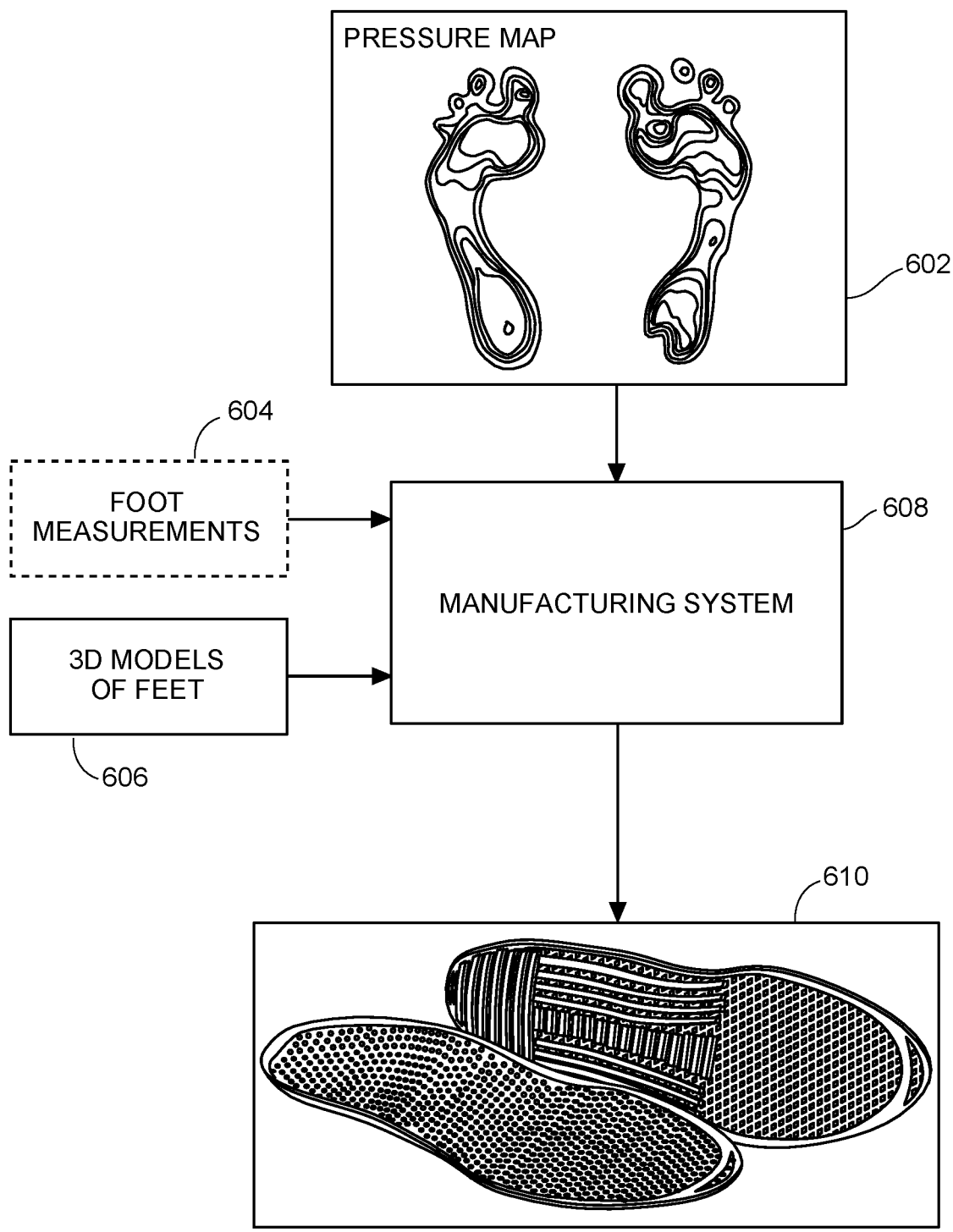
FIG. 6 shows a block diagram of one of the applications of the pressure maps generated by the pressure map prediction system for manufacturing custom in-soles in accordance with an embodiment.

FIG. 6 shows a block diagram of one of the applications of the pressure maps 602 generated by the pressure map prediction system 140 in accordance with an embodiment of the invention. The pressure map of the feet 602 is provided to a manufacturing system 608. In addition, foot measurements 604, which may be obtained from the generated structured 3D models of the feet 606, are also fed to the manufacturing system 608, alongside the structured 3D models of the feet 606. The manufacturing system 608, such as a 3D printer, can then output products, such as customized insoles 610. The output product (e.g., insoles 610) is made not only taking into consideration the provided measurements and object shape (e.g., shape of a person's feet), but it is also customized to the specific pressure points in the predicted pressure map 602. In the case of the insoles 610 of FIG. 6, the manufacturing system 608 provides a product that is a better ergonomic fit to the feet than the insoles that would be produced from foot measurements alone.

Training the Pressure Estimation Deep Learning Network (DLN)

A starting point for any machine learning method such as deep learning networks is a documented dataset containing multiple instances of system inputs and correct outcomes (i.e., the training data). This data set can be used, using methods known in the art, including but not limited to standardized machine learning methods such as parametric classification methods, non-parametric methods, decision tree learning, neural networks, methods combining both inductive and analytic learning, and modeling approaches such as regression models, to train the machine learning system and to evaluate and optimize the performance of the trained system. The quality of the output of the machine learning system output depends on (a) the pattern parameterization, (b) the learning machine design, and (c) the quality of the training database. These components can be refined and optimized using various methods. For example, the database can be refined by adding datasets for new documented subjects. The quality of the database can be improved, for example, by populating the database with cases in which the customization was accomplished by one or more experts. Thus, the database will better represent the expert's knowledge. In one embodiment, the database includes data for examples of matches, which can assist in the evaluation of a trained system. The training database can also be improved via a feedback method by populating the database with successful outcomes produced by the DLN being trained.

FIG. 7 shows a block diagram of the DLN training system 138 for training the object pressure estimation DLN via supervised learning in accordance with one embodiment. Supervised learning involves providing a learning rule to the network with a set of examples of desired network behavior.

The DLN training system 138, 710 can be coupled with a 3D scanner 701, such as a foot scanner, for 3D model generation, and an object pressure scanner 706 to generate corresponding pressure maps 708. The DLN training system 138, 710 includes a 3D model receiver 712, an object parameter receiver 714, a pressure map receiver 716, and a training database 718 to store the training data 720. The training data 720 is collected from a large number of sample objects associated with a particular object category (e.g., human foot) to train the object pressure estimation DLN 146, 226, 266 to generate a pressure map 152, 228, 268 of objects belonging to that particular object category. As mentioned above, different DLNs can be trained in generating pressure maps of objects of different categories.

An example of training the object pressure estimation DLN 722 for generating a foot pressure map is discussed below. The DLN training system 138, 710 is fed with training data 720 collected from the feet of a large number of people. For each person, the 3D model receiver 712 receives a 3D model 702 of the person's foot (or feet). The 3D models 702 are generated using a 3D scanner 701 (e.g., foot scanner). Alternatively, the received 3D models may be generated from a series of 2D images using the 3D model generation module 142, 210, 240. The object parameter receiver 714 receives the various parameters of the object or person as mentioned above, including height, weight, BMI, gender, racial profile, etc. Finally, the pressure map receiver 716 receives pressure maps 708 of objects (e.g., a person's feet) generated by the object pressure scanner 706. The samples are collected from thousands of people to populate the training database 718. The samples from the training database 718 are used to train and test the object pressure estimation DLN 722 to generate the pressure maps 152, 228, 268. Virtual training data may also be generated to train the pressure estimation DLN 146, 226, 266, 722 using techniques such as data augmentation on existing foot pressure scans, or generating virtual training data from virtual foot models.

Illustrative Keypoint DLN Architecture and Retopology Process

Figure 8:
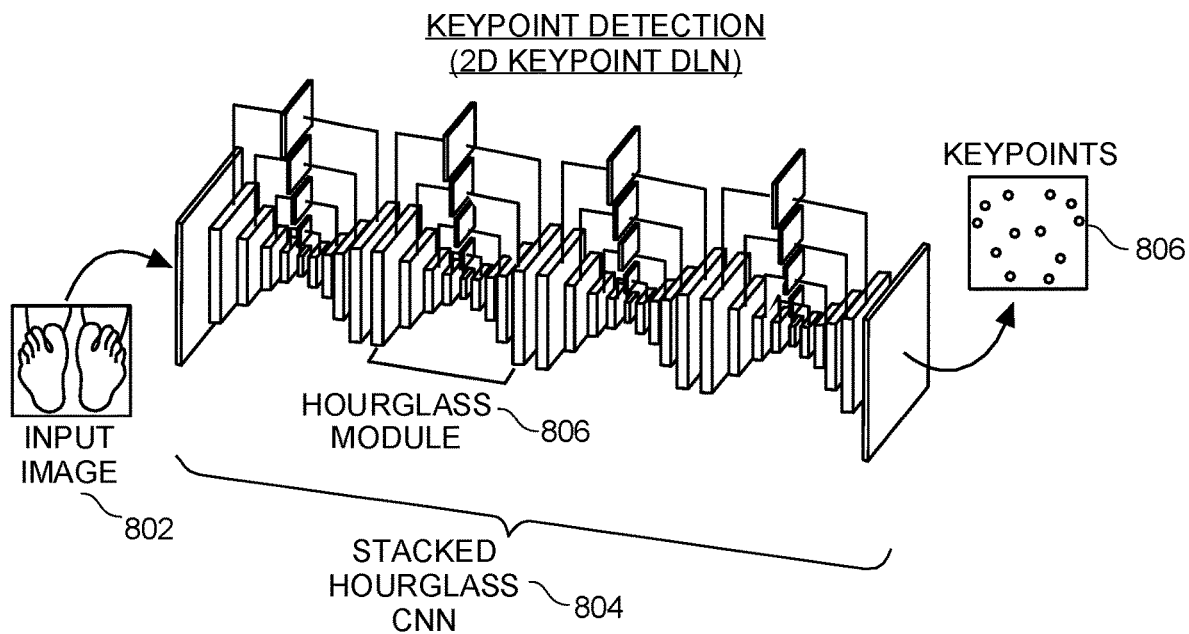
FIG. 8 shows a diagram of a 2D keypoint DLN architecture for detecting keypoints in 2D photographs using deep learning, according to one illustrative embodiment of the present invention.

FIG. 8 shows a diagram of a 2D keypoint DLN 244 architecture for detecting keypoints 246 in 2D photographs 236 using deep learning, according to one illustrative embodiment of the present invention. FIG. 8 shows an illustrative Stacked Hourglass Convolutional Neural Network (CNN) architecture.

Stacked Hourglass CNNs are landmark detection DLNs that are efficient in detecting patterns such as human pose. They are usually composed of multiple stacked hourglass modules, where each hourglass module has symmetric downsampling and upsampling layers. Consecutive hourglass modules have intermediate supervision, thus allowing for repeated inference between the downsampling and upsampling layers. In one embodiment, the Stacked Hourglass CNN algorithm is implemented as described in Alejandro Newell, et al., "Stacked Hourglass Networks for Human Pose Estimation," ECCV 2016, Sep. 17, 2016, available at arXiv: 1603.06937, which is hereby incorporated by reference in its entirety herein as if fully set forth herein.

FIG. 8 shows a Stacked Hourglass CNN 804 with four hourglass modules 806. As shown in FIG. 8, a trained stacked hourglass CNN may be used to extract keypoints 806 from an input image 802. To carry out 2D keypoint annotation, a Stacked Hourglass CNN must be trained beforehand using training data sets comprising object photos and corresponding keypoints. Such training data may be obtained through 3D scanned and retopologized object (e.g., foot) data.

The High-Resolution Network (HRNet) is another landmark detection DLN that is a suitable DLN base architecture for the 2D keypoint DLN 244. HRNet are used in human pose estimation, semantic segmentation, and facial landmark detection. HRNets are composed of connected parallel high-to-low resolution convolutions, allowing repeated fusions across parallel convolutions, and leading to strong high-resolution representations. In one embodiment, the HRNet algorithm is implemented as described in Ke Sun, et al., "Deep High-Resolution Representation Learning for Human Pose Estimation," CVPR 2019, Jan. 9, 2020, available at arXiv: 1902.09212, which is hereby incorporated by reference in its entirety herein as if fully set forth herein.

Stacked Hourglass CNNs and HRNets are only illustrative DLN algorithms that are within the scope of the present invention, and the present invention is not limited to the use of Stacked Hourglass CNNs or HRNets. Other DLN algorithms are also within the scope of the present invention. For example, in one embodiment of the present invention, a convolutional neural network (CNN) is utilized as a 2D keypoint DLN 244 to extract object keypoints 246 from 2D input photos 236.

Figure 9:
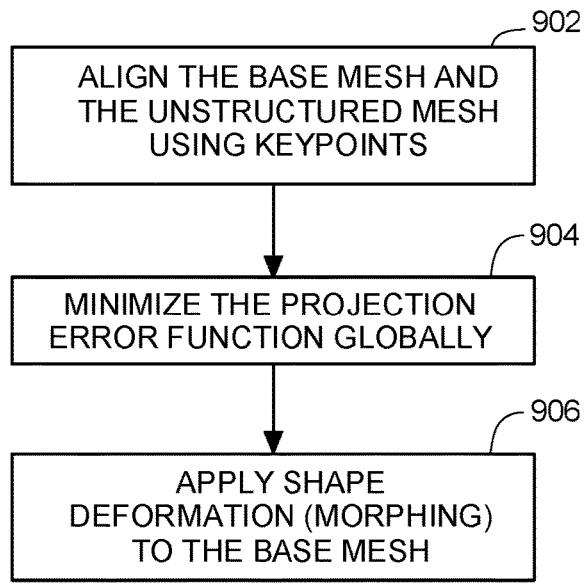
FIG. 9 shows a flowchart detailing an example of a retopology method for constructing a structured 3D model using a base mesh, according to one illustrative embodiment of the present invention.

FIG. 9 shows a flowchart detailing an example of a retopology 220, 256 method for constructing a structured 3D model 224, 260 from an annotated unstructured 3D mesh 218, 254 and a base 3D mesh 222, 258, according to one illustrative embodiment of the present invention. The base 3D mesh 222, 258 is a raw 3D mesh representation of the object that is stored on a server (e.g., in the cloud) or within the device. The retopology process 220, 256 can access a library of 3D base meshes containing at least one base 3D mesh 222, 258 in the category of the target object 133. In one embodiment, the base 3D meshes in the library are structured and pre-annotated. Retopology 220, 256 is a morphing process that morphs an existing structured and annotated base 3D mesh 222, 258 into a structured 3D model 224, 260 of the target object 133 so that its keypoints and its surface match the keypoints and surface of the annotated unstructured 3D mesh 218, 254.

Retopology 220, 256 is therefore an adaptive base mesh adjustment process, as shown in FIG. 9. This process has three major steps. First, in step 902, the keypoints of the base mesh 222, 258 and the unstructured mesh 218, 254 are aligned. Second, in step 904, a new 3D position for each of the keypoints of the base mesh 222, 258 is computed such that a 3D projection error function is minimized. The projection error function is a measure of the deformation, or distance, between the base mesh 222, 258 and the unstructured 3D mesh 218, 254 (i.e., the target mesh), and has at least two terms. The first term of the projection error function is a surface error corresponding to a distance between the surface of the base mesh and the surface of the target mesh. The second term of the projection error function is a keypoint projection error corresponding to a global distance metric between the base mesh keypoints and the target mesh keypoints. The two terms may be weighted in the projection error function using coefficients. Step 904 leads to the definition of a modified set of estimated 3D keypoints for the base mesh. Third, in step 906, the base mesh is deformed (i.e., morphed) to match its modified 3D keypoints. The minimization of the projection error function insures an adhesion of the base mesh to the surface of the target mesh. The morphing of the base mesh 222, 258 results in a scaled and structured 3D mesh representation of the object 133 (i.e., the structure 3D model 224, 260).

Another embodiment of retopology may use the input 2D images 236 directly. In that embodiment, keypoints are used for the initial alignment of each of an input image 236 with a projection of the base mesh 258 onto the image plane. A different projection error function may be used here to capture the contour error (i.e., the difference in shape between the image of the object and the base mesh projection). In order to minimize the projection error, the surface of the base mesh is morphed so that its projected contour matches the shape of the object 133 on the image 236. Both retopology methods described above can be used iteratively, where the error function is computed for several iterations of the morphed base mesh until a low enough error threshold is achieved.

According to one embodiment, the morphing of structured 3D base meshes through projection error minimization to generate structured 3D models improves on existing photogrammetry processes, and allows for the 3D reconstruction of the object's 3D model using as little as 4-6 photos, in some embodiments, instead of typical photogrammetry processes that might require 40-60 photos.

Pressure Estimation DLN Architecture

Figure 10:
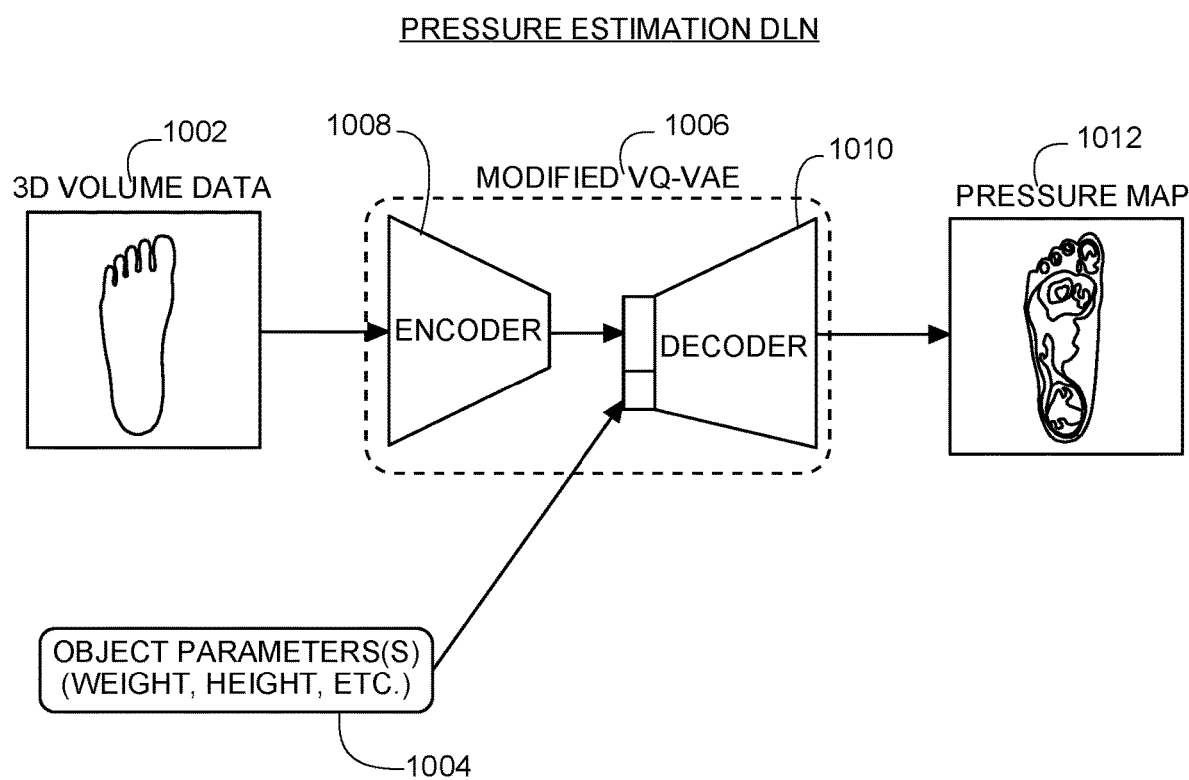
FIG. 10 shows a block diagram of a pressure map prediction DLN architecture, according to one illustrative embodiment of the present invention.

FIG. 10 shows a block diagram of a pressure estimation DLN architecture, according to one illustrative embodiment of the present invention. The embodiment of FIG. 10 shows a pressure estimation DLN architecture that is based on a Vector Quantised-Variational AutoEncoder (VQ-VAE).

A Variational AutoEncoder (VAE) consists of an encoder neural network, a decoder neural network, and a loss function. The encoder encodes the data to a latent representation (i.e., a hidden representation) which is effectively a reduced-dimension stochastic representation of the data. The decoder then creates a reconstructed representation with the same dimensions as the data. The loss function (i.e., the function that is optimized in the training process) is designed to enable the VAE to learn the stochastic distribution of the input and take it into consideration in the reconstruction process. This design allows the VAE to construct complex generative models of data and fit them to large datasets, leading to efficient image generation and reinforcement learning. The Vector Quantised-Variational AutoEncoder (VQ-VAE) differs from the VAE in that the latent representation is discrete, rather than continuous, leading to a generative network model that learns discrete representations.

In FIG. 10, the DLN architecture is a modified VQ-VAE 1006 with additional parameter inputs 1004 to the latent representation, where the additional parameter inputs 1004 are one or more received object parameters 120, 136, 208, 238. In FIG. 10, the input of the VQ-VAE is 3D volume data 1002, denoting the generated structured 3D model 224 of the target object 133 (FIG. 2A) or a density map 264 derived from the structured 3D model 260 (FIG. 2B). As for any VQ-VAE, the modified VQ-VAE 1006 has an encoder network 1008 and a decoder network 1010. However, the latent representation is modified by the inclusion of object parameters 1004. The VQ-VAE decoder generates the estimated pressure map 1012 of the target object 133. Adding the object parameters to the latent representation enables the VQ-VAE to learn different representations from different object parameters, hence taking into account the object parameters in the generation of the estimated pressure map 1012.

In one embodiment, the VQ-VAE algorithm upon which the DLN of FIG. 10 is based is implemented as described in Aaron van den Oord, et al., "Neural Discrete Representation Learning," NIPS 2017, Dec. 5, 2017, available at arXiv: 1711.00937, which is hereby incorporated by reference in its entirety herein as if fully set forth herein. The VQ-VAE is only illustrative DLN algorithms that are within the scope of the present invention, and the present invention is not limited to the use of VQ-VAEs. Other DLN algorithms are also within the scope of the present invention.

Hardware, Software, and Cloud Implementation of the Present Invention

As discussed, the data (e.g., photos, textual descriptions, and the like) described throughout the disclosure can include data that is stored on a database stored or hosted on a cloud computing platform. It is to be understood that although this disclosure includes a detailed description on cloud computing, below, implementation of the teachings recited herein are not limited to a cloud computing environment. Rather, embodiments of the present invention are capable of being implemented in conjunction with any other type of computing environment now known or later developed.

Cloud computing can refer to a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics may include one or more of the following. On-demand self-service: a cloud consumer can unilaterally provision computing capabilities, such as server time and network storage, as needed automatically without requiring human interaction with the service's provider. Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time. Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

In another embodiment, Service Models may include one or more of the following. Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models may include one or more of the following. Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

The cloud computing environment may include one or more cloud computing nodes with which local computing devices used by cloud consumers, such as, for example, personal digital assistant (PDA) or cellular telephone, desktop computer, laptop computer, and/or automobile computer system can communicate. Nodes can communicate with one another. They can be group physically or virtually, in one or more networks, such as Private, Community, Public, or Hybrid clouds as described hereinabove, or a combination thereof. This allows cloud computing environment to offer infrastructure, platforms and/or software as services for which a cloud consumer does not need to maintain resources on a local computing device. It is understood that the types of computing devices are intended to be exemplary only and that computing nodes and cloud computing environment can communicate with any type of computerized device over any type of network and/or network addressable connection (e.g., using a web browser).

Figure 11:
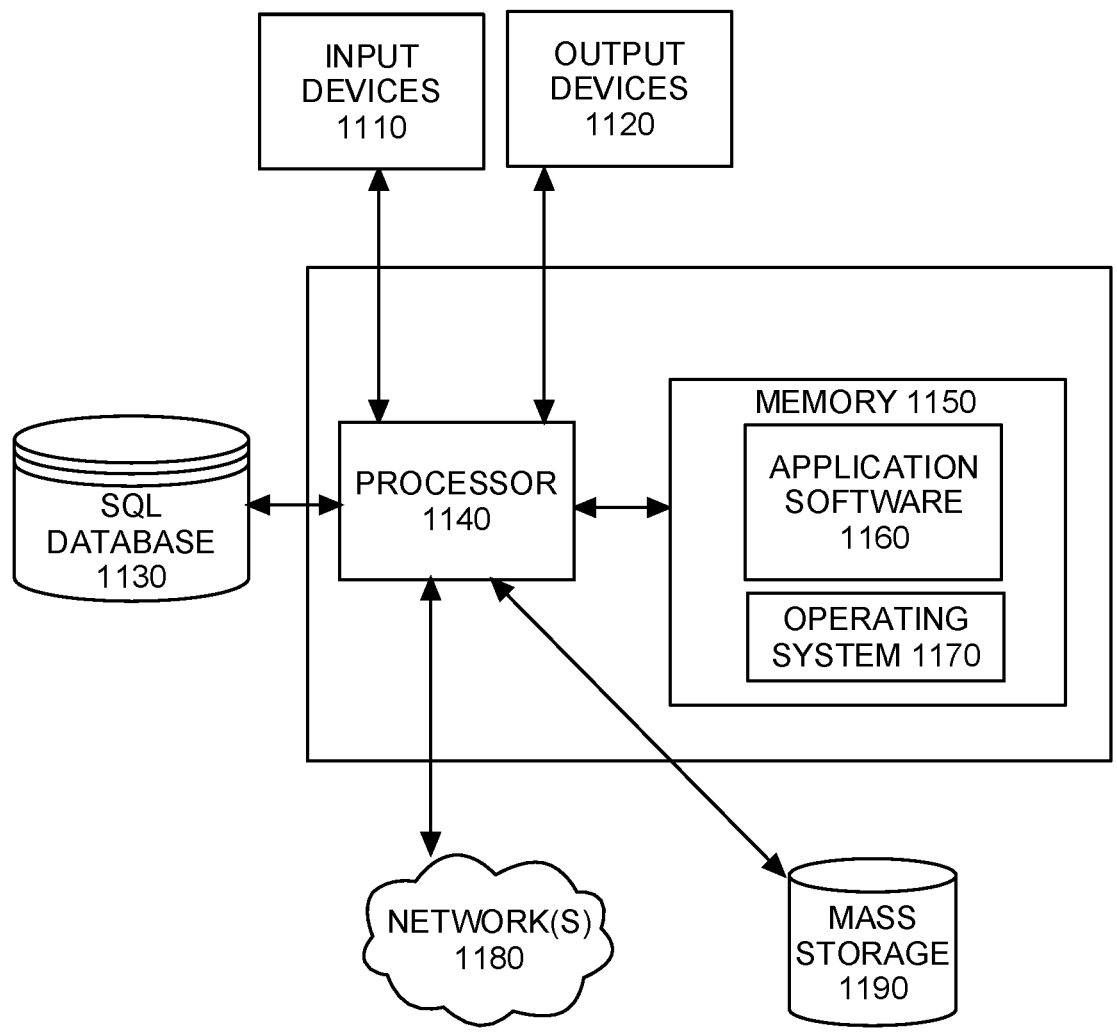
FIG. 11 shows an illustrative hardware architecture diagram of a server for implementing one embodiment of the present invention.

The present invention may be implemented using server-based hardware and software. FIG. 11 shows an illustrative hardware architecture diagram of a server for implementing one embodiment of the present invention. Many components of the system, for example, network interfaces etc., have not been shown, so as not to obscure the present invention. However, one of ordinary skill in the art would appreciate that the system necessarily includes these components. A user-device is a hardware that includes at least one processor 1140 coupled to a memory 1150. The processor may represent one or more processors (e.g., microprocessors), and the memory may represent random access memory (RAM) devices comprising a main storage of the hardware, as well as any supplemental levels of memory e.g., cache memories, non-volatile or back-up memories (e.g. programmable or flash memories), read-only memories, etc. In addition, the memory may be considered to include memory storage physically located elsewhere in the hardware, e.g. any cache memory in the processor, as well as any storage capacity used as a virtual memory, e.g., as stored on a mass storage device.

The hardware of a user-device also typically receives a number of inputs 1110 and outputs 1120 for communicating information externally. For interface with a user, the hardware may include one or more user input devices (e.g., a keyboard, a mouse, a scanner, a microphone, a web camera, etc.) and a display (e.g., a Liquid Crystal Display (LCD) panel). For additional storage, the hardware may also include one or more mass storage devices 1190, e.g., a floppy or other removable disk drive, a hard disk drive, a Direct Access Storage Device (DASD), an optical drive (e.g. a Compact Disk (CD) drive, a Digital Versatile Disk (DVD) drive, etc.) and/or a tape drive, among others. Furthermore, the hardware may include an interface one or more external SQL databases 1130, as well as one or more networks 1180 (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces to communicate with each other.

The hardware operates under the control of an operating system 1170, and executes various computer software applications 1160, components, programs, codes, libraries, objects, modules, etc. indicated collectively by reference numerals to perform the methods, processes, and techniques described above.

Figure 12:
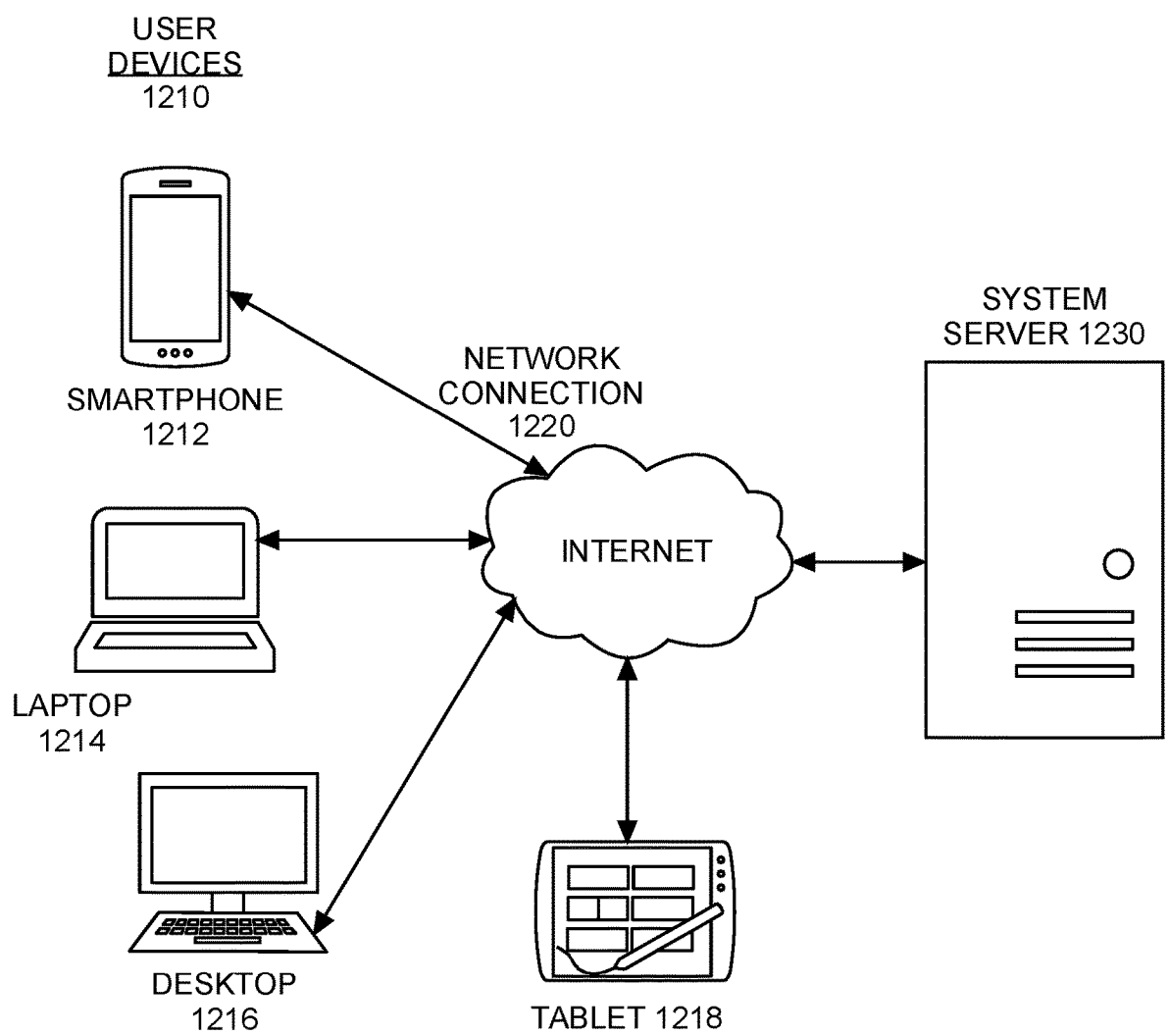
FIG. 12 shows an illustrative system architecture for implementing one embodiment of the present invention.

The present invention may be implemented in a client server environment. FIG. 12 shows an illustrative system architecture for implementing one embodiment of the present invention in a client server environment. User devices 1210 on the client side may include smart phones 1212, laptops 1214, desktop PCs 1216, tablets 1210, or other devices. Such user devices 1210 access the service of the system server 1230 through some network connection 1220, such as the Internet.

In some embodiments of the present invention, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service) and increases user satisfaction and ease of use. Various business models, revenue models, and delivery mechanisms for the present invention are envisioned, and are all to be considered within the scope of the present invention.

In general, the method executed to implement the embodiments of the invention, may be implemented as part of an operating system or a specific application, component, program, object, module or sequence of instructions referred to as "computer program(s)" or "computer code(s)." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), and digital and analog communication media.

Example Use Cases of the Present Invention

FIGS. 13A, 13B, 14A, 14B, and 15 are illustrative diagrams of a use case of the present invention in which a mobile device with a single camera and an AR guided scan application 102, 132, 202, 232 is used as an interface for pressure map prediction, showing mobile graphical user interfaces (GUIs) through which some embodiments of the present invention have been implemented.

FIG. 13A is an illustrative diagram of the mobile device GUI showing user instructions for object selection. In the example of FIG. 13A, the object is a human foot, and the GUI shows user instructions to select the right or left foot. FIG. 13B shows an illustrative diagram of the mobile device GUI for sending images of the object (i.e., the selected foot) to the pressure map prediction system 140.

Figure 14A:
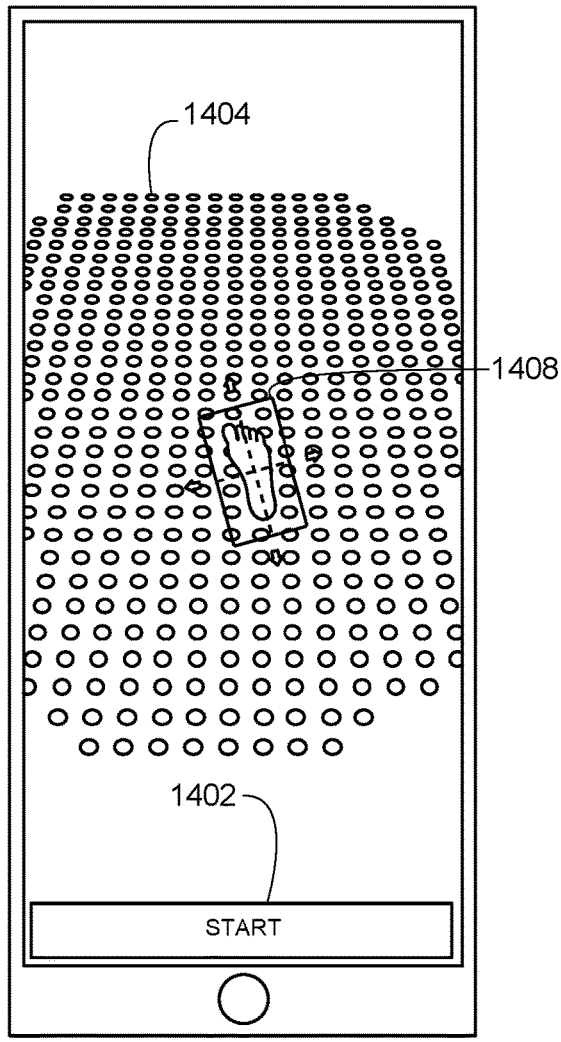
Figure 14B:
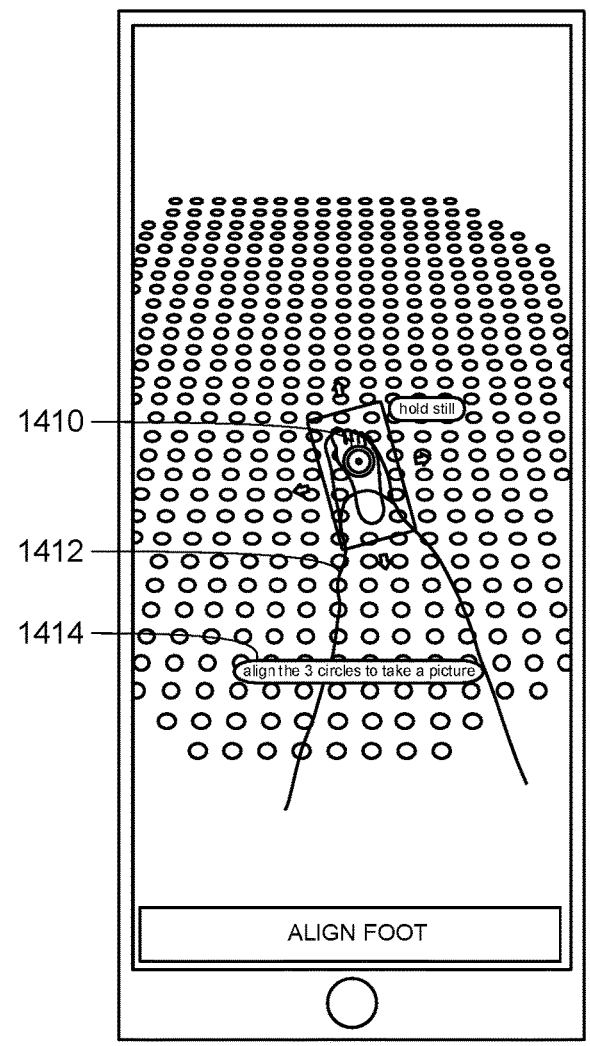
Figure 15:
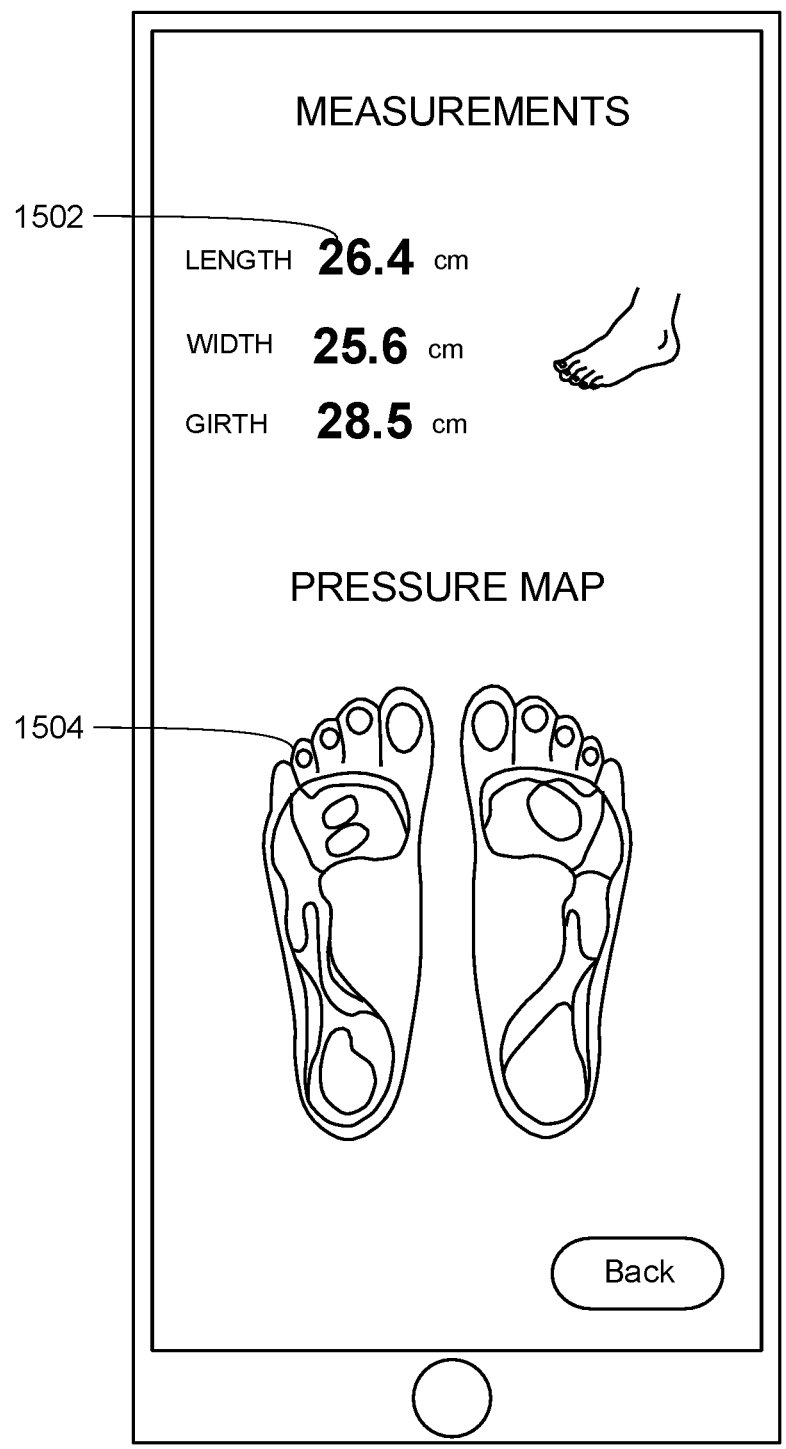

FIG. 14A shows an illustrative diagram of the mobile device GUI for capturing the selected object (i.e., the user's right foot). The capture process may be initiated by the user through pressing a "start" button 1402. The GUI shows an illustrative target object position (e.g., a footprint) 1408 and a detected surface representation 1404 overlaid in augmented reality (AR) over the real-time image captured by the camera. FIG. 14B shows an illustrative diagram of the mobile device GUI for object alignment, where the AR target object position (e.g., a footprint) 1408 and surface representation 1404 are still apparent. FIG. 14B shows the object (the user's right foot) 1412 being guided by AR object trackers 1410 on the mobile device GUI. User instructions 1414 may pop up to further guide the user's movements and actions. An image may be captured automatically once the object 1412 is aligned with the AR target position 1408. FIG. 15 shows an illustrative diagram of the mobile device GUI with the output object (i.e., feet) pressure map prediction 1504 and measurements 1502.

FIGS. 13A, 13B, 14A, 14B, and 15 are illustrative diagrams of a use case of the present invention in which a single camera on a mobile device is used to capture 2D photos for object pressure map prediction. The mobile device shown in FIGS. 13A, 13B, 14A, 14B, and 15 comprises at least one camera, a processor, a non-transitory storage medium, and a wireless communication to a server (not shown). In one embodiment, the hardware architecture of the mobile device and the server are as shown in FIGS. 11 and 12. In one embodiment, the 2D photos of the object are transmitted to a server that performs the operations described herein. In one embodiment, the photos of the object are analyzed locally by the processor of the mobile device. The operations performed return one or more pressure map predictions, which may be stored on the server, as well as presented to the user, as shown in FIG. 15. In addition, the pressure map predictions may then be utilized for many purposes, including but not limited to, offering for sale to the subject one or more custom garments, custom body suites, custom braces (e.g., medical prosthetics), custom PPE (personal protection equipment), and so on. Further, the pressure map predictions may be output to a third-party mobile device and/or a third-party server. In one embodiment, the output may be in the form of a digital file, an email, a textual description on a mobile application or website, a text message, combinations thereof, and the like.

Without loss of generality, the pressure map predictions may be output, transmitted, and/or utilized for any purpose for which a pressure map is useful. In particular, the pressure map predictions may be output to a computing device and/or a corresponding server, for example associated with a company that manufactures garments or equipment based on the pressure map. One of ordinary skill in the art would recognize that the output of the pressure map predictions may be utilized for any purpose in which accurate and simple pressure maps are useful, such as but not limited to retail, manufacturing, medicine, and so forth.

In conclusion, the present invention is expected to use as little as 2-6 photos and achieve useful and accurate pressure map predictions. The system does not require the use of any specialized hardware sensors, does not require users to stand over any special surface or against any special background, does not require special lighting, and can be used with photos taken at any distance. The result is a pressure map prediction system that works with any mobile device so that users can easily take photos of an object and benefit from automatic pressure map predictions.

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with the other activities, postponed, delayed, and continued after a time gap, such that every user is accommodated to practice the methods of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A computer-implemented method for generating a pressure map of an object, the computer-implemented method executable by a hardware processor, the method comprising:
   receiving a plurality of 2-dimensional (2D) images of the object, wherein the plurality of 2D images capture the object from different angles;
   receiving one or more input parameters, the input parameters comprising at least one attribute related to the object;
   constructing a structured 3-dimensional (3D) model of the object from the plurality of 2D images; and
   generating the pressure map of the object from the structured 3D model and the input parameters using a pressure estimation deep learning network (DLN), wherein the pressure estimation DLN is trained to generate pressure maps of objects from a given structured 3D model and given parameters of a given object, wherein the pressure map comprises a pressure profile comprising a plurality of pressure points, each pressure point indicating a level of pressure where the object is in contact with a surface, wherein the pressure estimation DLN predicts the level of pressure at the plurality of pressure points.

2. The computer-implemented method of claim 1, wherein constructing the structured 3D model of the object from the plurality of 2D images comprises:
   generating a scaled unstructured 3D mesh of the object from the plurality of 2D images using a photogrammetry process and a scale factor, wherein the scaled unstructured 3D mesh is utilized to generate the structured 3D model.

3. The computer-implemented method of claim 2, wherein constructing the structured 3D model of the object from the plurality of 2D images further comprises:
   generating the structured 3D model from an annotated scaled unstructured 3D mesh by morphing an annotated structured base 3D mesh to match the annotated scaled unstructured 3D mesh.

4. The computer-implemented method of claim 3, wherein constructing the structured 3D model of the object from the plurality of 2D images further comprises:
   utilizing a 3D keypoint DLN to generate the annotated scaled unstructured 3D mesh of the object from the scaled unstructured 3D mesh of the object, wherein the annotated scaled unstructured 3D mesh is utilized to generate the structured 3D model.

5. The computer-implemented method of claim 4, wherein the 3D keypoint DLN is based on a PointNet.

6. The computer-implemented method of claim 3, wherein constructing the structured 3D model of the object from the plurality of 2D images further comprises:
   utilizing a 2D keypoint DLN to extract one or more keypoints from the plurality of 2D images, wherein the one or more keypoints are used to generate the annotated unstructured 3D mesh in order to generate the structured 3D model.

7. The computer-implemented method of claim 6, wherein constructing the structured 3D model of the object from the plurality of 2D images further comprises:
   projecting the one or more keypoints onto the scaled unstructured 3D mesh of the object to generate the annotated scaled unstructured 3D mesh, wherein the annotated scaled unstructured 3D mesh is utilized to generate the structured 3D model.

8. The computer-implemented method of claim 6, wherein the 2D keypoint DLN is selected from the group consisting of a stacked hourglass network and a high-resolution network (HRNet).

9. The computer-implemented method of claim 1, wherein generating the pressure map of the object from the structured 3D model and the input parameters further comprises:
generating a density map by projecting the structured 3D model onto the surface, wherein the density map is utilized to generate the pressure map.

10. The computer-implemented method of claim 9,
wherein the pressure estimation DLN is a modified vector quantized-variational auto- encoder (VQ-VAE),
wherein the density map is utilized as input to the modified VQ-VAE to generate the pressure map, and
wherein the modified VQ-VAE is trained to generate a given pressure map from a given density map and one or more given input parameters.

11. The computer-implemented method of claim 1, wherein the one or more input parameters comprise at least a scale factor, and wherein the scale factor is used to scale the structured 3D model to real-world coordinates.

12. The computer-implemented method of claim 1, further comprising:
providing instructions to manufacture a 3D product from the structured 3D model utilizing 3D measurements extracted from the structured 3D model.

13. The computer-implemented method of claim 1, wherein the object is a body part.

14. The computer-implemented method of claim 1, wherein the pressure estimation DLN is trained on training data comprising structured 3D models from a 3D scanner and corresponding pressure maps from an object pressure sensor.

15. A non-transitory storage medium for storing program code, the program code executable by a hardware processor, the program code when executed by the hardware processor causing the hardware processor to generate a pressure map of an object, the program code comprising code to:
receive a plurality of 2-dimensional (2D) images of the object, wherein the plurality of 2D images capture the object from different angles;
receive one or more input parameters, the input parameters comprising at least one attribute related to the object;
construct a structured 3-dimensional (3D) model of the object from the plurality of 2D images; and
generate the pressure map of the object from the structured 3D model and the input parameters using a pressure estimation deep learning network (DLN), wherein the pressure estimation DLN is trained to generate pressure maps of objects from a given structured 3D model and given parameters of a given object, wherein the pressure map comprises a pressure profile comprising a plurality of pressure points, each pressure point indicating a level of pressure where the object is in contact with a surface, wherein the pressure estimation DLN predicts the level of pressure at the plurality of pressure points.

16. The non-transitory storage medium of claim 15, wherein the program code to construct the structured 3D model of the object from the plurality of 2D images comprises code to:
generate a scaled unstructured 3D mesh of the object from the plurality of 2D images using a photogrammetry process and a scale factor, wherein the scaled unstructured 3D mesh is utilized to generate the structured 3D model.

17. The non-transitory storage medium of claim 16, wherein the program code to construct the structured 3D model of the object from the plurality of 2D images further comprises code to:
generate the structured 3D model from an annotated scaled unstructured 3D mesh by morphing an annotated structured base 3D mesh to match the annotated scaled unstructured 3D mesh.

18. The non-transitory storage medium of claim 17, wherein the program code to construct the structured 3D model of the object from the plurality of 2D images further comprises code to:
utilize a 3D keypoint DLN to generate the annotated scaled unstructured 3D mesh of the object from the scaled unstructured 3D mesh of the object, wherein the annotated scaled unstructured 3D mesh is utilized to generate the structured 3D model.

19. The non-transitory storage medium of claim 17, wherein the program code to construct the structured 3D model of the object from the plurality of 2D images further comprises code to:
utilize a 2D keypoint DLN to extract one or more keypoints from the plurality of 2D images, wherein the one or more keypoints are used to generate the annotated unstructured 3D mesh in order to generate the structured 3D model.

20. A system comprising a hardware processor and a non-transitory storage medium for storing program code, the program code executable by the hardware processor, the program code when executed by the hardware processor causing the hardware processor to generate a pressure map of an object, the program code comprising code to:
receive a plurality of 2-dimensional (2D) images of the object, wherein the plurality of 2D images capture the object from different angles;
receive one or more input parameters, the input parameters comprising at least one attribute related to the object;
construct a structured 3-dimensional (3D) model of the object from the plurality of 2D images; and
generate the pressure map of the object from the structured 3D model and the input parameters using a pressure estimation deep learning network (DLN), wherein the pressure estimation DLN is trained to generate pressure maps of objects from a given structured 3D model and given parameters of a given object, wherein the pressure map comprises a pressure profile comprising a plurality of pressure points, each pressure point indicating a level of pressure where the object is in contact with a surface, wherein the pressure estimation DLN predicts the level of pressure at the plurality of pressure points.

* * * * *